US012778527B2

(12) United States Patent
Horiuchi et al.

(10) Patent No.: US 12,778,527 B2
(45) Date of Patent: Nov. 3, 2026

(54) RADIATION IRRADIATION APPARATUS AND RADIOGRAPHY SYSTEM

(71) Applicant: FUJIFILM CORPORATION, Tokyo (JP)

(72) Inventors: Hisatsugu Horiuchi, Kanagawa (JP); Masayoshi Matsuura, Kanagawa (JP); Kyohei Mori, Kanagawa (JP); Tomoaki Nakashima, Kanagawa (JP); Akihito Bettoyashiki, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 112 days.

(21) Appl. No.: 18/939,552

(22) Filed: Nov. 7, 2024

(65) Prior Publication Data

US 2025/0160774 A1 May 22, 2025

(30) Foreign Application Priority Data

Nov. 20, 2023 (JP) ................................ 2023-196964

(51) Int. Cl.
*A61B 6/00* (2024.01)
*A61B 6/10* (2006.01)

(52) U.S. Cl.
CPC ............ *A61B 6/4452* (2013.01); *A61B 6/105* (2013.01); *A61B 6/4411* (2013.01)

(58) Field of Classification Search
None
See application file for complete search history.

(56) References Cited

U.S. PATENT DOCUMENTS

2012/0148031 A1* 6/2012 Eaves .................. A61B 6/4405 378/198
2015/0023475 A1* 1/2015 Gordon ................ A61B 6/4405 378/195

(Continued)

FOREIGN PATENT DOCUMENTS

DE 102009010602 A1 * 9/2010 ........... A61B 6/4411
EP 1506741 A1 * 2/2005 ......... A61B 17/2255

(Continued)

OTHER PUBLICATIONS

Translation of de102009010602 (Year: 2009).*

(Continued)

*Primary Examiner* — David J Makiya
*Assistant Examiner* — Soorena Kefayati
(74) *Attorney, Agent, or Firm* — SOLARIS Intellectual Property Group, PLLC

(57) ABSTRACT

A radiation irradiation apparatus that is configured to independently travel from a decubitus table on which a subject can be placed, the radiation irradiation apparatus including: an attachment portion that allows the radiation irradiation apparatus to be attached to and detached from the decubitus table; a radiation irradiation portion capable of emitting radiation to the subject; a holding portion that is provided at a distal end portion thereof with the radiation irradiation portion and that holds the radiation irradiation portion to be displaceable; and a restriction mechanism that restricts displacement of the holding portion, in which the radiation irradiation apparatus is attached to the decubitus table through the attachment portion to release restriction of the displacement in the restriction mechanism.

8 Claims, 12 Drawing Sheets

(56) References Cited

U.S. PATENT DOCUMENTS

| | | | | |
|---|---|---|---|---|
| 2015/0124939 | A1* | 5/2015 | Ahn | A61B 6/4452<br>378/167 |
| 2015/0305699 | A1* | 10/2015 | Sakuragi | A61B 6/4405<br>250/493.1 |
| 2018/0108447 | A1* | 4/2018 | Turner | A61B 6/4405 |
| 2018/0222044 | A1* | 8/2018 | Guerrera | A61B 6/0407 |
| 2019/0290230 | A1* | 9/2019 | Keil | A61B 6/4085 |
| 2019/0388040 | A1* | 12/2019 | Vancamberg | A61B 6/0414 |
| 2020/0060638 | A1* | 2/2020 | Assolari | A61B 6/04 |
| 2020/0163634 | A1* | 5/2020 | Turner | A61B 6/4441 |
| 2021/0121145 | A1* | 4/2021 | Turner | A61B 6/02 |

FOREIGN PATENT DOCUMENTS

| | | | | | |
|---|---|---|---|---|---|
| JP | 2011136028 | A | * | 7/2011 | A61B 6/588 |
| JP | 2012050523 | A | * | 3/2012 | |
| JP | 2015-208573 | A | | 11/2015 | |

OTHER PUBLICATIONS

Translation of ep1506741 (Year: 2004).*
Translation of jp2011136028 (Year: 2011).*
Translation of jp2012050523 (Year: 2012).*

* cited by examiner

RADIATION IRRADIATION APPARATUS AND RADIOGRAPHY SYSTEM

CROSS-REFERENCE TO RELATED APPLICATIONS

The present application claims priority under 35 U.S.C. § 119 to Japanese Patent Application No. 2023-196964, filed on Nov. 20, 2023. The above application is hereby expressly incorporated by reference, in its entirety, into the present application.

BACKGROUND

1. Technical Field

The technology of the present disclosure relates to a radiation irradiation apparatus and a radiography system.

2. Description of the Related Art

JP2011-136028A discloses a radiography apparatus including a radiation source that outputs radiation, a radiation source main body portion that accommodates the radiation source, a radiation detector that detects the radiation transmitted through a subject and converts the detected radiation into a radiation image in a case in which the radiation source irradiates the subject with the radiation, a cassette main body portion that transmits the radiation and accommodates the radiation detector, and an attachment mechanism that is attached to the radiation source main body portion and is attachable to and detachable from the cassette main body portion or is attachable to and detachable from an imaging table on which the cassette main body portion is disposed.

JP2015-208573A discloses a radiation generation apparatus including a radiation generation unit that generates radiation, a support unit that supports the radiation generation unit, a power supply unit that supplies power to the radiation generation unit, and a moving unit that is provided with the power supply unit and is movable, in which the moving unit is attachable to and detachable from the support unit.

JP2012-50523A discloses a radiation mobile examination cart including a radiation irradiation section that irradiates a subject with radiation from radiation generation unit, a movement section that moves the radiation irradiation section along a predetermined guide, an adjustment section that adjusts an irradiation angle of the radiation to be emitted from the radiation generation unit so that the radiation is radiated to a radiation detection section that moves in a direction opposite to the movement direction of the radiation detection section, in accordance with the movement of the radiation irradiation section by the movement section, and detects the radiation emitted from the radiation irradiation section and transmitted through the subject, and a control section that controls the radiation irradiation section to emit the radiation and controls the radiation detection section to detect the radiation, in synchronization with an irradiation operation of irradiating the radiation from the radiation irradiation section and a detection operation of detecting the radiation by the radiation detection section.

SUMMARY

JP2011-136028A discloses a technique of fixing a radiation source main body portion that accommodates a radiation source to an imaging table through an attachment mechanism. On the other hand, JP2015-208573A and JP2012-50523A disclose a radiography apparatus including a moving mechanism capable of moving a radiation source with respect to a subject.

However, the techniques of JP2011-136028A, JP2015-208573A, and JP2012-50523A do not consider the displacement of the holding portion provided with the radiation irradiation portion in a state in which the radiation irradiation apparatus that has a radiation source and is capable of traveling is attached to the decubitus table. Therefore, according to the technique of the present disclosure, there is provided a radiation irradiation apparatus that is capable of displacing a holding portion in which a radiation irradiation portion is provided in a state in which a posture of the radiation irradiation apparatus is stable, and a radiography system.

A first aspect according to the technology of the present disclosure relates to a radiation irradiation apparatus that is capable of traveling independently from a decubitus table on which a subject can be placed, including: an attachment portion that allows the radiation irradiation apparatus to be attached to and detached from the decubitus table; a radiation irradiation portion capable of emitting radiation to the subject; a holding portion that is provided at a distal end portion thereof with the radiation irradiation portion and that holds the radiation irradiation portion to be displaceable; and a restriction mechanism that restricts displacement of the holding portion, in which the radiation irradiation apparatus is attached to the decubitus table through the attachment portion to release restriction of the displacement in the restriction mechanism.

A second aspect according to the technology of the present disclosure is the radiation irradiation apparatus according to the first aspect, in which the displacement includes movement of the holding portion including a component in an up-down direction.

A third aspect according to the technique of the present disclosure is the radiation irradiation apparatus according to the first aspect, in which the displacement includes movement of the holding portion including a component in a horizontal direction.

A fourth aspect according to the technique of the present disclosure is the radiation irradiation apparatus according to the first aspect, in which the displacement includes rotation of the holding portion in a case in which the radiation irradiation apparatus is viewed from above.

A fifth aspect according to the technology of the present disclosure is the radiation irradiation apparatus according to the first aspect, in which the restriction mechanism includes an engaging member that is engageable with the holding portion, and the restriction of the displacement is released by engagement of the engaging member with the holding portion in conjunction with an attachment operation through the attachment portion.

A sixth aspect according to the technology of the present disclosure relates to the radiation irradiation apparatus according to the fifth aspect, in which the decubitus table includes a guide mechanism that allows the radiation irradiation apparatus attached to the attachment portion to be movable with respect to the decubitus table, the guide mechanism includes a guide rail extending along a movement direction of the radiation irradiation apparatus, and a moving member that is movable along the guide rail, the attachment portion is attached to the moving member, and a release member provided in the moving member directly or indirectly displaces the engaging member to release the engagement of the engaging member with the holding portion.

A seventh aspect according to the technology of the present disclosure is the radiation irradiation apparatus according to the first aspect, further comprising a detection portion capable of detecting a state in which the attachment portion is attached to the decubitus table, in which the restriction mechanism is capable of releasing restriction of the displacement in a case in which the detection portion detects that the attachment portion is attached to the decubitus table.

An eighth aspect according to the technology of the present disclosure is the radiation irradiation apparatus according to the first aspect, in which the attachment portion has a plurality of contact portions, and the plurality of contact portions support a rotational moment of the radiation irradiation apparatus in a falling direction in a state in which the radiation irradiation apparatus is attached to the decubitus table through the attachment portion.

A ninth aspect according to the technology of the present disclosure is the radiation irradiation apparatus according to the eighth aspect, in which the decubitus table is provided with a support member to which the attachment portion is attachable, and the attachment portion is attached to the support member by sandwiching the support member from an up-down direction through the plurality of contact portions.

A tenth aspect according to the technology of the present disclosure is a radiography system comprising the radiation irradiation apparatus according to the first aspect, and a decubitus table to which the radiation irradiation apparatus is attachable.

According to the technology of the present disclosure, there is provided a radiation irradiation apparatus that is capable of displacing a holding portion in which a radiation irradiation portion is provided in a state in which a posture of the radiation irradiation apparatus is stable, and a radiography system.

DETAILED DESCRIPTION

An example of an embodiment of a radiography system 10 according to the technique of the present disclosure will be described with reference to the accompanying drawings.

In the following description, for convenience of description, a front-rear direction (also referred to as a depth direction), a width direction, and a height direction of the radiography system 10 are indicated by three arrows X, Y, and Z. First, the height direction is indicated by an arrow Z, an arrow Z direction indicated by the arrow Z is defined as an upper direction of the radiography system 10, and an opposite direction thereof is defined as a lower direction. The up-down direction corresponds to a vertical direction. The width direction is indicated by an arrow X orthogonal to the arrow Z, a direction indicated by the arrow X is defined as a front direction of the radiography system 10, and a direction opposite to the front direction is defined as a rear direction. A direction orthogonal to the arrow Z and the arrow X is indicated by an arrow Y in the right-left direction, a direction indicated by the arrow Y is defined as a left direction of the radiography system 10, and the opposite direction is defined as a right direction. In addition, in the following description, the expression using the side, such as an upper side, a lower side, a left side, a right side, a front side, and a rear side, has the same meaning as the expression using the direction.

In the present embodiment, a "vertical direction" refers not only to a perfect vertical direction but also to a vertical direction in the sense of including an error that is generally acceptable in the technical field to which the technology of the present disclosure belongs and that does not contradict the concept of the technology of the present disclosure. In addition, similarly, "horizontal direction" refers to the horizontal direction in the sense of including an error generally allowed in the technical field to which the technology of the present disclosure belongs, that is, an error to the extent that it does not contradict the gist of the technology of the present disclosure, in addition to the exact horizontal direction.

First Embodiment

Figure 1:
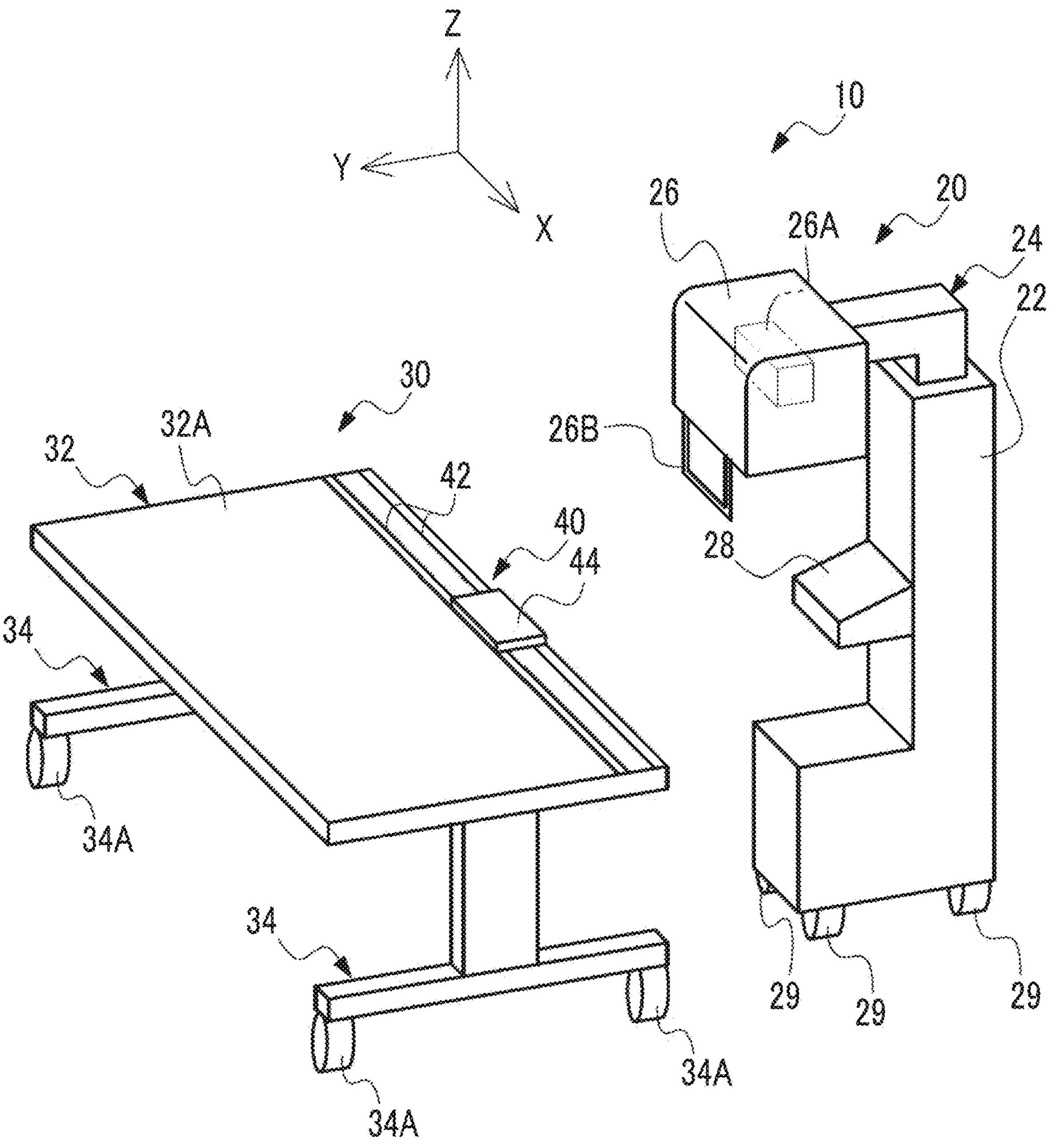
FIG. 1 is a schematic perspective view illustrating an example of a configuration of a radiography system according to an embodiment.
Figure 2:
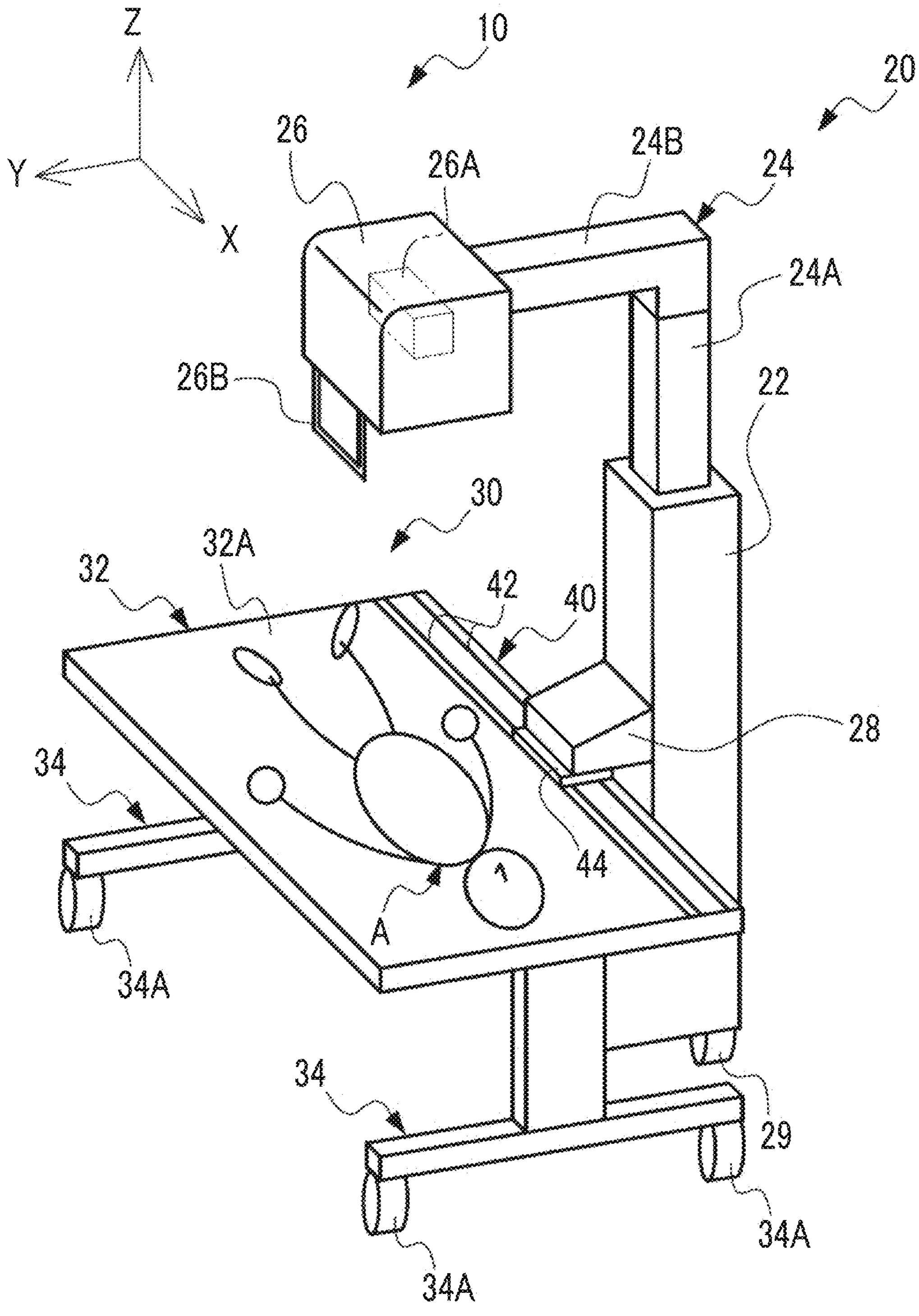
FIG. 2 is a schematic perspective view illustrating an example of the configuration of the radiography system according to the embodiment.

As shown in FIG. 1 as an example, a radiography system 10 is a system that performs radiography on a subject A (see FIG. 2). The radiography system 10 includes a radiation source unit 20 and a decubitus table 30. The radiation source unit 20 is a device that comprises a radiation source 26A and irradiates the subject A with radiation (for example, X-rays or gamma rays) generated from the radiation source 26A. The decubitus table 30 is a table on which the subject A can be placed. In a state in which the subject A is placed on the decubitus table 30, the subject A is irradiated with radiation, and radiography is performed. The radiography system 10 is an example of a "radiography system" according to the technology of the present disclosure. The radiation source unit 20 is an example of a "radiation irradiation apparatus" according to the technology of the present disclosure. The decubitus table 30 is an example of a "decubitus table" according to the technology of the present disclosure.

The radiation source unit 20 comprises a main body portion 22, an arm 24, and a radiation irradiation portion 26. The main body portion 22 is a portion forming a body portion of the radiation source unit 20, and accommodates a power source system that supplies power to the radiation source 26A inside, a control device that controls the entire radiation source unit 20, a mechanism for driving the arm 24, and the like. The arm 24 is an example of a "holding portion" according to the technique of the present disclosure.

The arm 24 is a part extending from the main body portion 22, and a proximal end side thereof is attached to the main body portion 22. The radiation irradiation portion 26 is provided in a distal end portion of the arm 24. The arm 24 is allowed to be displaced to move the radiation irradiation portion 26 with respect to the subject A. That is, the arm 24 holds the radiation irradiation portion 26 in a displaceable manner. Specifically, the arm 24 can be expanded and contracted in the up-down direction. In addition, the arm 24 can be expanded and contracted in the horizontal direction. With this configuration, the radiation irradiation portion 26 can be moved with respect to the subject A through the arm 24. The arm 24 is an example of an "arm" according to the technology of the present disclosure.

In the example shown in FIG. 1, the arm 24 extends from an upper surface of the main body portion 22. Specifically, the arm 24 has an L-shape having a part extending along an up-down direction from an upper surface of the main body portion 22 and a part bent from an upper end of the part and extending along a right-left direction. That is, the arm 24 comprises a vertical portion 24A along the up-down direction and a horizontal portion 24B extending from an upper end of the vertical portion 24A in the right-left direction. Here, although a form example has been described in which the arm 24 has an L-shape, this is merely an example. The arm 24 may be a C-shaped arm as viewed from the front-rear direction or may be an arm having a plurality of joints.

The radiation irradiation portion 26 is configured to irradiate the subject A with radiation. The radiation irradiation portion 26 is attached to a distal end of the arm 24. The radiation source 26A is accommodated in the radiation irradiation portion 26. An irradiation direction of the radiation generated in the radiation source 26A is defined by an irradiation field limiter (not shown) inside the radiation source 26A. Then, the radiation source 26A emits radiation to the subject A. In the example illustrated in FIG. 1, the radiation irradiation portion 26 emits radiation downward. The radiation irradiation portion 26 is an example of a "radiation irradiation portion" according to the technique of the present disclosure.

In addition, the radiation irradiation portion 26 comprises a gripping portion 26B. The gripping portion 26B is a portion that can be gripped by a user (for example, a radiologist or a doctor) of the radiography system 10. The user can move the radiation irradiation portion 26 with respect to the decubitus table 30 by gripping the gripping portion 26B.

The attachment portion 28 is provided in an intermediate portion of the main body portion 22 in an up-down direction. The attachment portion 28 is a portion to which the radiation source unit 20 can be attached to and detached from the decubitus table 30. That is, the radiation source unit 20 is attached to the decubitus table 30 through the attachment portion 28. In the example shown in FIG. 1, the attachment portion 28 is a portion that protrudes from a left side surface of the main body portion 22. The position where the attachment portion 28 is provided is merely an example, and the attachment portion 28 may be provided on the front side surface or the rear side surface of the main body portion 22. Details of the attachment portion 28 will be described later. The attachment portion 28 is an example of an "attachment portion" according to the technique of the present disclosure.

In addition, wheels 29 are provided on the lower surface of the main body portion 22. The radiation source unit 20 can travel independently with respect to the decubitus table 30 through the wheels 29 provided in the main body portion 22. The radiation source unit 20, for example, may travel through the wheels 29 by being pushed by the user, or may travel by receiving power from a power source (for example, a motor) (not shown) to rotate the wheels 29. In the example shown in FIG. 1, the wheels 29 are provided at four corners of the lower surface of the main body portion 22. The wheel 29 is, for example, a caster.

The decubitus table 30 comprises a placement portion 32, a leg portion 34, and a guide mechanism 40. The placement portion 32 is a flat plate-shaped portion on which the subject A is placed. In the example shown in FIG. 1, the placement portion 32 has a rectangular parallelepiped shape having a front-rear direction as a longitudinal direction. The placement portion 32 has a placement surface 32A on which the subject A is placed, on an upper side. That is, the placement surface 32A has a rectangular parallelepiped shape in a plan view. The decubitus table 30 is, for example, a dedicated bed for radiography. The decubitus table 30 is provided with a radiation detector (not shown), detects radiation emitted from the radiation source 26A and transmitted through a part of the subject A to be diagnosed, and outputs a radiation image. The radiation detector is referred to as a flat panel detector (FPD).

In addition, leg portions 34 are provided on the lower surface of the placement portion 32. The leg portions 34 are members that support the placement portion 32. The placement portion 32 is set to a predetermined height from the floor surface by the leg portions 34. In the example shown in FIG. 1, the leg portions 34 are provided at both ends of the placement portion 32 in the front-rear direction, respectively. Wheels 34A are provided in the pair of leg portions 34, respectively. In the example shown in FIG. 1, one wheel 34A is provided at each of both end portions of the leg portion 34 in the right-left direction. The decubitus table 30 can be moved by the wheels 34A. The decubitus table 30 may be configured to have no wheel 34A and be fixed to a floor surface.

The guide mechanism 40 is a mechanism that allows the radiation source unit 20 attached through the attachment portion 28 to be movable with respect to the decubitus table 30. Specifically, the guide mechanism 40 is a mechanism for guiding the movement along one side of the placement surface 32A of the radiation source unit 20. The guide mechanism 40 is an example of a "guide mechanism" according to the technique of the present disclosure.

More specifically, the guide mechanism 40 is provided in the placement portion 32. The guide mechanism 40 comprises a pair of guide rails 42 and a stage member 44 guided by the pair of guide rails 42. In the example shown in FIG. 1, the guide mechanism 40 is provided at a right end portion of the placement surface 32A of the placement portion 32. The pair of guide rails 42 extend along the longitudinal direction (here, the front-rear direction) of the placement surface 32A, and the stage member 44 is freely movable along the longitudinal direction of the placement surface 32A along the guide rails 42. That is, the movement direction of the radiation source unit 20 by the guide mechanism 40 is along the longitudinal direction of the placement surface 32A. The pair of guide rails 42 is an example of a "guide rail" according to the technique of the present disclosure, and the stage member 44 is an example of a "moving member" according to the technique of the present disclosure.

Figure 3:
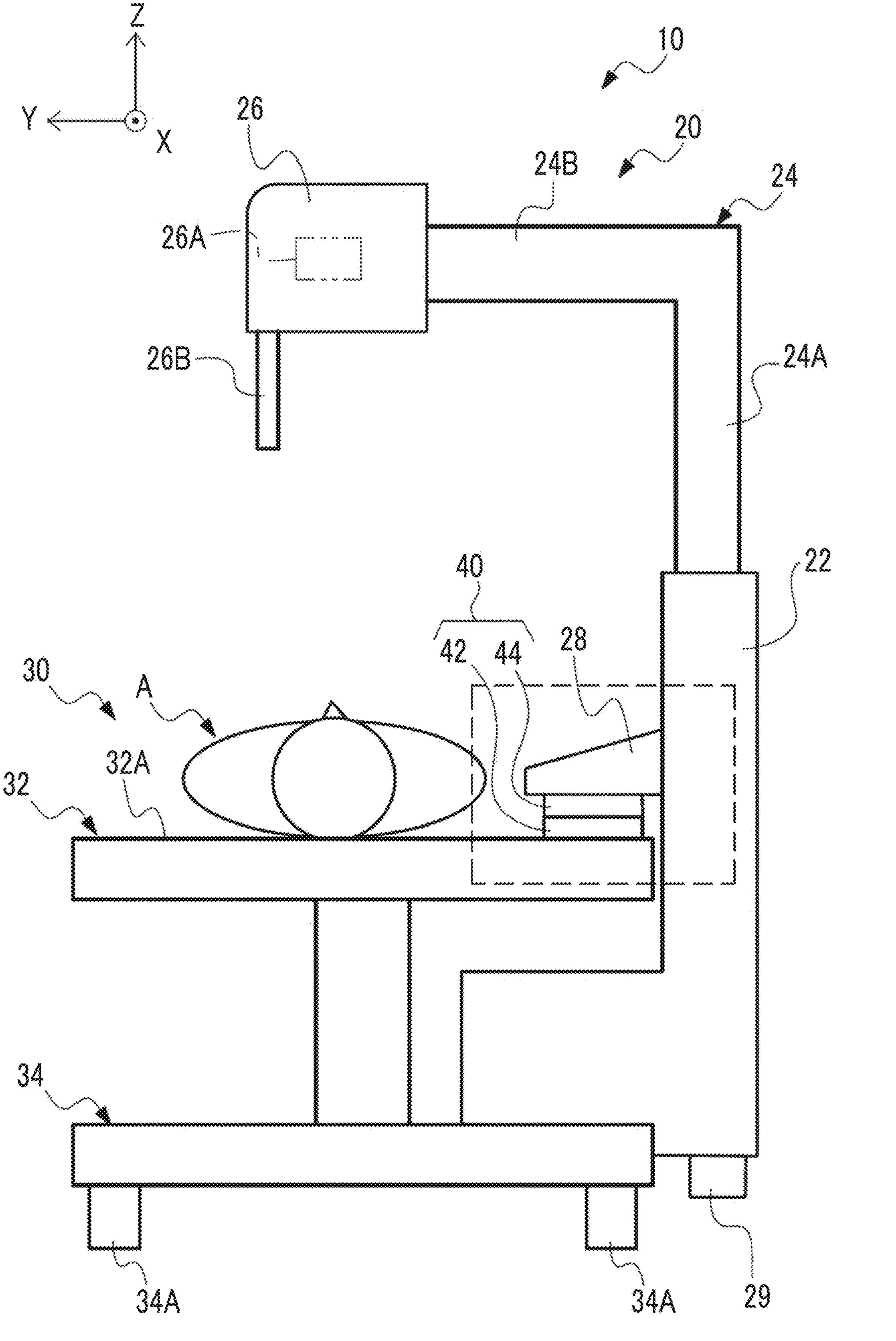
FIG. 3 is a schematic front view illustrating an example of the configuration of the radiography system according to the embodiment.

As shown in FIGS. 2 and 3 as an example, radiography is performed on a subject A placed on the decubitus table 30. In this case, the arm 24 is displaced in order to dispose the radiation source 26A at a predetermined position with respect to the subject A. Specifically, the arm 24 is extended upward with respect to the main body portion 22 or is extended toward the side of the decubitus table 30 (here, toward the left side). As a result, the radiation source 26A is disposed at a predetermined position with respect to the subject A.

Here, in a case in which the arm 24 is displaced in order to move the radiation source 26A, the radiation irradiation portion 26 is also moved accordingly. The radiation irradiation portion 26 is provided with various mechanisms and electronic devices in addition to the radiation source 26A. Therefore, the centroid of the radiation source unit 20 also moves with the movement of the radiation irradiation portion 26. For example, in a case in which the arm 24 is extended for radiography and the radiation source 26A is positioned above the decubitus table 30, the centroid of the radiation source unit 20 is moved above the decubitus table 30 and to the decubitus table 30 side (here, the left side). Therefore, it is considered that the centroid of the radiation source unit 20 is separated from the main body portion 22, and the posture of the radiation source unit 20 is unstable (for example, the radiation source unit 20 is likely to fall or waver during movement). In particular, since the radiation source unit 20 according to the present embodiment can travel through the wheels 29, the influence of the instability is larger than that of a stationary radiation irradiation apparatus fixed to a floor surface, a ceiling, or the like.

Therefore, in the radiography system 10 according to the present embodiment, in a case in which radiography is performed, the radiation source unit 20 is attached to the decubitus table 30 through the attachment portion 28. In a case in which the radiography is performed, the radiation source 26A is positioned above the decubitus table 30 in a state in which the radiation source unit 20 is attached to the decubitus table 30. Since the decubitus table 30 has a sufficient weight with respect to the radiation source unit 20 and the position of the centroid is low, the posture of the radiation source unit 20 is stabilized even in a case where the arm 24 is displaced by attaching the radiation source unit 20 to the decubitus table 30.

In addition, the radiation source unit 20 attached to the decubitus table 30 can be moved by the guide mechanism 40. Specifically, the radiation source unit 20 is attached to the stage member 44 through the attachment portion 28. Then, the stage member 44 is moved along the guide rail 42, so that the radiation source unit 20 is also moved along the decubitus table 30. In the example shown in FIG. 2, the radiation source unit 20 is movable along the front-rear direction.

On the other hand, there is a case where radiography is performed in a state in which the radiation source unit 20 is not attached to the decubitus table 30. For example, a case where the radiation source 26A of the radiation source unit 20 horizontally irradiates the subject A in a standing state with radiation is exemplified. In this case, a detector unit (not shown) is disposed at a position facing the radiation source unit 20. Then, the radiation that has passed through the subject A is detected by the radiation detector provided in the detector unit. In such an imaging method, the radiation source unit 20 is independent of the decubitus table 30, and the posture of the radiation source unit 20 is destabilized in a case in which the arm 24 is displaced. Therefore, it is necessary to suppress the inadvertent displacement of the arm 24. In addition, even in a case in which the radiation source unit 20 is caused to travel independently of the decubitus table 30 (for example, in a case in which the radiation source unit 20 is moved from the vicinity of the decubitus table 30 to another place), it is necessary to suppress the inadvertent displacement of the arm 24 in the same manner.

Figure 4:
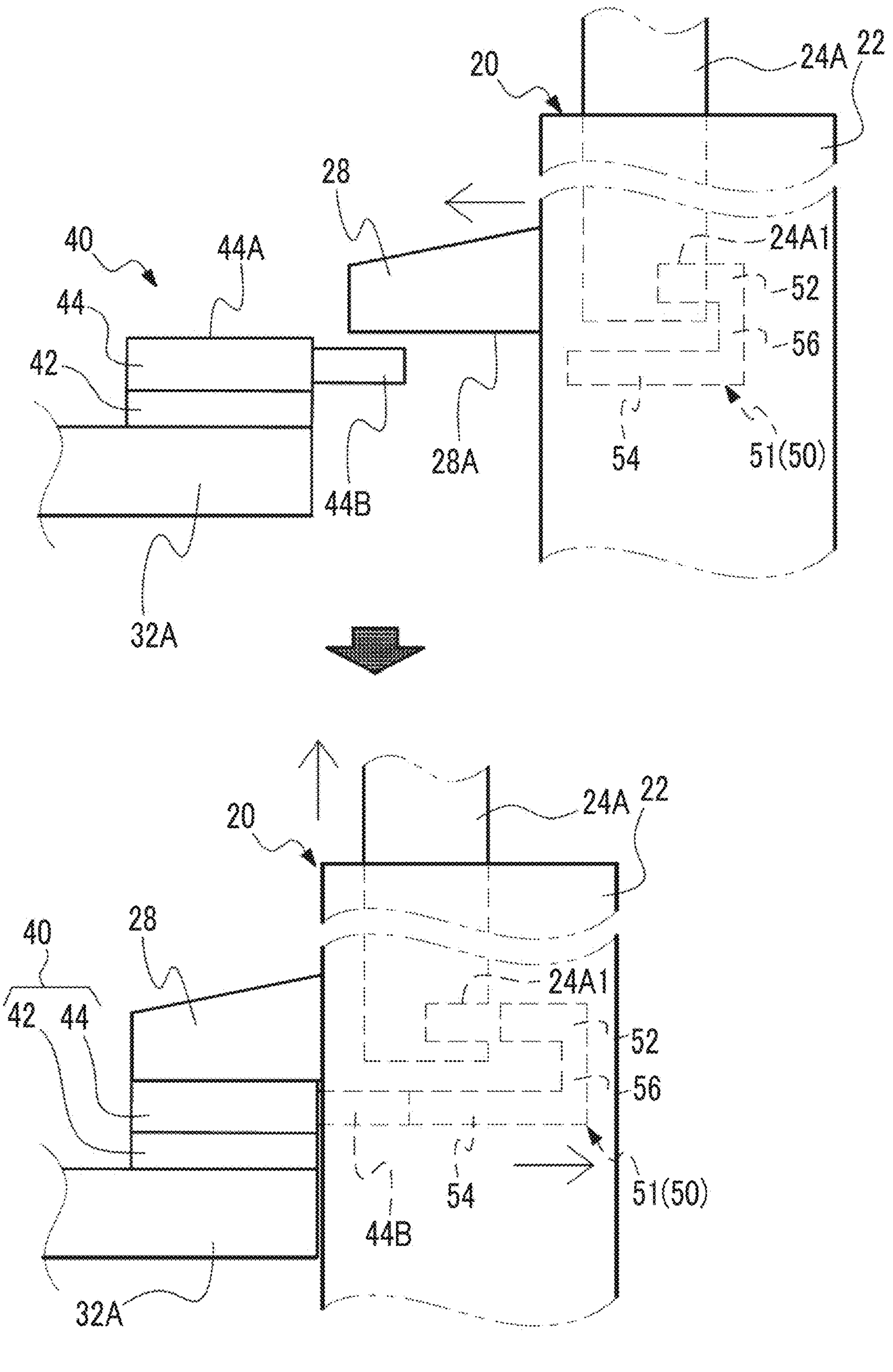
FIG. 4 is a partially enlarged view illustrating an example of the configuration of the radiography system according to the embodiment.

Therefore, as shown in FIG. 4 as an example, the radiation source unit 20 according to the present embodiment comprises a restriction mechanism 50 that restricts the displacement of the arm 24. FIG. 4 is a partially enlarged view of the dotted line frame in FIG. 3. The restriction mechanism 50 includes an engaging member 51. The engaging member 51 is a member that can be engaged with the arm 24 and restricts the displacement of the arm 24 by being engaged with the arm 24. Here, the engagement includes coming into contact with the arm 24 in an aspect capable of restricting the displacement of the arm 24. Specifically, a part of the engaging member 51 is inserted into the arm 24 from a direction intersecting with the direction in which the arm 24 is displaced, so that the displacement of the arm 24 is restricted. Hereinafter, in the present embodiment, the displacement of the arm 24 will be described as an example of the expansion and contraction of the arm 24 in the up-down direction. The restriction mechanism 50 is an example of a "restriction mechanism" according to the technique of the present disclosure, and the engaging member 51 is an example of an "engaging member" according to the technique of the present disclosure.

In the example shown in the upper part of FIG. 4, the engaging member 51 comprises an engaging portion 52, an abutting portion 54, and a connecting portion 56. The engaging portion 52 and the abutting portion 54 are a pair of rod-shaped members that are arranged in the up-down direction and extend along a right-left direction, and the connecting portion 56 is a member that connects the engaging portion 52 and the abutting portion 54 in the up-down direction. The abutting portion 54 is positioned below the vertical portion 24A of the arm 24 and is a portion that can abut with a release pin 44B, which will be described later. In addition, the engaging portion 52 is a portion engageable with the arm 24. The connecting portion 56 is positioned on the right side of the arm 24 and connects a right end portion of the engaging portion 52 to a right end portion of the abutting portion 54.

Here, the engaging member 51 is biased in a direction (here, the left direction) toward the arm 24 by a biasing member (for example, a spring member) (not shown). In addition, a hole 24A1 is formed in a lower end of the vertical portion 24A of the arm 24. Then, the engaging portion 52 of the engaging member 51 is inserted into the hole 24A1, so that the expansion and contraction of the arm 24 in the up-down direction is restricted. That is, even in a case where the arm 24 is displaced in the up-down direction, the engaging portion 52 comes into contact with the inner peripheral surface of the hole 24A1 to restrict the expansion and contraction of the arm 24 in the up-down direction. In such a manner, in a state in which the radiation source unit 20 is not attached to the decubitus table 30, the displacement of the arm 24 is restricted by the restriction mechanism 50 in the radiation source unit 20.

Next, a description will be made of a state in which the radiation source unit 20 is attached to the decubitus table 30 with reference to FIG. 4. In a case where the radiation source unit 20 is attached to the decubitus table 30, the radiation source unit 20 is moved toward the decubitus table 30 at a position where the attachment portion 28 faces the stage member 44. In the example shown in the upper part of FIG. 4, the radiation source unit 20 is moved in the left direction. Then, as shown in a lower part of FIG. 4, the attachment portion 28 is attached to the stage member 44. Specifically, the lower surface 28A of the attachment portion 28 is placed on the upper surface 44A of the stage member 44, whereby the radiation source unit 20 is attached to the decubitus table 30.

The restriction on the displacement of the arm 24 by the restriction mechanism 50 is released by attaching the radiation source unit 20 to the decubitus table 30 through the attachment portion 28. Specifically, the restriction on the displacement of the arm 24 is released by releasing the engagement between the arm 24 and the engaging member 51 in conjunction with the attachment operation through the attachment portion 28.

In the example shown in a lower part of FIG. 4, the release pin 44B is provided in the stage member 44. The release pin 44B is a rod-shaped member that protrudes from a surface (here, a right side surface) of the stage member 44 on the radiation source unit 20 side. In a state where the attachment portion 28 is placed on the stage member 44, the release pin 44B is inserted into the radiation source unit 20. The distal end of the release pin 44B abuts on the abutting portion 54 of the engaging member 51. Accordingly, the engaging member 51 is displaced. In the example shown in the lower part of FIG. 4, the entire engaging member 51 is moved in the pressing direction (here, the right direction) by the release pin 44B. The release pin 44B is an example of a "release member" according to the technique of the present disclosure.

The engagement between the engaging member 51 and the arm 24 is released with the displacement of the engaging member 51. Specifically, since the engaging member 51 moves in the right direction, the engaging portion 52 also moves in the right direction together with the engaging member 51. Accordingly, since the engaging portion 52 is detached from the hole 24A1 of the arm 24, the arm 24 can be displaced in the up-down direction. In this way, the restriction on the displacement of the arm 24 is released in conjunction with the attachment operation through the attachment portion 28. The user displaces the arm 24 (here, expands and contracts in the up-down direction) to move the radiation irradiation portion 26 to a position predetermined with respect to the subject A. The arm 24 may be manually expanded and contracted in the up-down direction by the user, or may be expanded and contracted in the up-down direction by a driving mechanism (for example, a power source such as a motor and a feeding screw mechanism that is operated by receiving power generated by the power source) (not shown).

As described above, the radiation source unit 20 according to the present embodiment includes the attachment portion 28, the radiation irradiation portion 26, the arm 24, and the restriction mechanism 50. A radiation irradiation portion 26 is provided at a distal end portion of the arm 24. In addition, the arm 24 is allowed to be displaced to move the radiation irradiation portion 26 with respect to the decubitus table 30. The restriction mechanism 50 restricts the displacement of the arm 24. Then, the radiation source unit 20 is attached to the decubitus table 30 through the attachment portion 28, so that the restriction on the displacement of the arm 24 by the restriction mechanism 50 is released. Here, in the imaging in the state in which the subject A is placed on the decubitus table 30 (that is, decubitus imaging), the arm 24 is displaced (for example, extended in the vertical direction) in order to adjust the position of the radiation source 26A. In the present configuration, since the radiation source unit 20 can travel independently of the decubitus table 30, the centroid moves upward and the posture becomes unstable in a case where the arm 24 is extended. Therefore, it is considered to attach the radiation source unit 20 to the decubitus table 30 and perform the decubitus imaging, but the arm 24 may be displaced before being attached to the decubitus table 30.

In the present configuration, the restriction mechanism 50 that restricts the displacement of the arm 24 is provided, and the restriction on the displacement of the arm 24 by the restriction mechanism 50 is released by attaching the arm 24 to the decubitus table 30 through the attachment portion 28. Therefore, it is realized that the arm 24 is displaced in a stable state of the radiation source unit 20.

For example, in the decubitus imaging, in a case where the radiation source unit 20 is not attached to the decubitus table 30 to stabilize the radiation source unit 20, it is considered that the lower centroid is achieved by increasing the size of the lower part of the radiation source unit 20 in order to correspond to the displacement of the arm 24. In this case, it is necessary to secure a large space around the decubitus table 30, and the radiation source unit 20 itself is also increased in size. In the present configuration, the size of the radiation source unit 20 can be reduced, and the space around the decubitus table 30 can be saved.

In addition, for example, in a case in which the radiation source unit 20 is caused to travel independently of the decubitus table 30 or an imaging method (for example, the standing imaging performed on the subject A in the standing state) that does not require the arm 24 to be extended is performed, the displacement of the arm is restricted. Therefore, the arm is suppressed from being inadvertently displaced. As described above, in the present configuration, it is possible to contribute to stabilization of the posture of the radiation source unit 20 in accordance with the imaging method.

In addition, in the radiation source unit 20 according to the present embodiment, the displacement of the arm 24 includes the expansion and contraction of the arm 24 including a component in an up-down direction. In a case in which the arm 24 expands and contracts in the up-down direction, the centroid of the radiation source unit 20 moves in the up-down direction, and the posture of the radiation source unit 20 may be unstable. In the present configuration, the restriction on the displacement of the arm 24 by the restriction mechanism 50 is released by attaching the arm 24 to the decubitus table 30 through the attachment portion 28. Therefore, it is realized that the arm 24 is expanded and contracted in a direction including a component in the up-down direction in a stable state of the radiation source unit 20.

In addition, in the radiation source unit 20 according to the present embodiment, the restriction mechanism 50 comprises an engaging member 51 that can be engaged with the arm 24. Then, the engaging member 51 releases the engagement with the arm 24 in conjunction with the attachment operation of the radiation source unit 20 through the attachment portion 28, so that the restriction on the displacement of the arm 24 is released. Accordingly, the burden of the operation of the user is reduced as compared with a case where the attachment operation and the operation of releasing the restriction by the restriction mechanism 50 are separate from each other. That is, it is not necessary to confirm the release of the restriction of the arm 24 after the attachment operation. In addition, since the restriction is released by the mechanical component in conjunction with the attachment operation, it is not necessary to dispose an expensive sensor or wiring in the radiation source unit 20, and the configuration of the radiation source unit 20 is reduced in cost.

In addition, in the radiography system 10 according to the present embodiment, the guide mechanism 40 that allows the radiation source unit 20 to be movable with respect to the decubitus table 30 is provided in the decubitus table 30. The guide mechanism 40 comprises a pair of guide rails 42 extending along the movement direction of the radiation source unit 20 and a stage member 44 that is movable along the guide rails 42. The attachment portion 28 of the radiation source unit 20 is attached to the stage member 44. The release pin 44B is provided in the stage member 44. The release pin 44B displaces the engaging member 51, so that the engagement between the arm 24 and the engaging member 51 is released. Since the stage member 44 can be moved along the guide rail 42, a position where the attachment portion 28 is attached can be changed within a movement range of the stage member 44. Therefore, the degree of freedom of selecting the position where the displacement of the arm 24 is released from the restriction is improved as compared with a case in which the restriction of the arm 24 is always released at the same position.

In the first embodiment, the aspect in which the expansion and contraction of the arm 24 in the up-down direction is restricted has been described as an example, but the technology of the present disclosure is not limited to this. For example, the engaging member 51 of the restriction mechanism 50 may restrict the expansion and contraction of the arm 24 in the horizontal direction or the rotation of the arm 24 in the horizontal plane (for example, the rotational movement of the horizontal portion 24B about the vertical portion 24A as a rotation axis). In this case, the engaging member 51 of the restriction mechanism 50 may be provided inside the arm 24, and power may be transmitted to the engaging member 51 by a wire that is disposed inside the arm 24 from the main body portion 22. In addition, the displacement of the arm 24 restricted by the engaging member 51 of the restriction mechanism 50 may be any one of the expansion and contraction of the arm 24 in the up-down direction, the expansion and contraction of the arm 24 in the horizontal direction, and the rotation of the arm 24, or a combination of two or more of the expansion and contraction of the arm 24 in the up-down direction, the expansion and contraction of the arm 24 in the horizontal direction, and the rotation of the arm 24.

In addition, in the first embodiment, the form example has been described in which the restriction mechanism 50 includes the engaging member 51, but the technology of the present disclosure is not limited to this. For example, in the restriction mechanism 50, the engaging member 51 may be indirectly displaced by a member that transmits the pressing force from the release pin 44B. That is, the restriction mechanism 50 may be an aspect in which the restriction mechanism 50 includes a plurality of members in addition to the engaging member 51 and the restriction of the arm 24 is released by interlocking the plurality of members.

Second Embodiment

In the first embodiment, the form example has been described in which the restriction by the restriction mechanism 50 is released by the displacement of the engaging member 51 in conjunction with the attachment operation, but the technology of the present disclosure is not limited to this. In the present second embodiment, the restriction by the restriction mechanism 50 is released according to the detection result of the detection portion 66.

Figure 5:
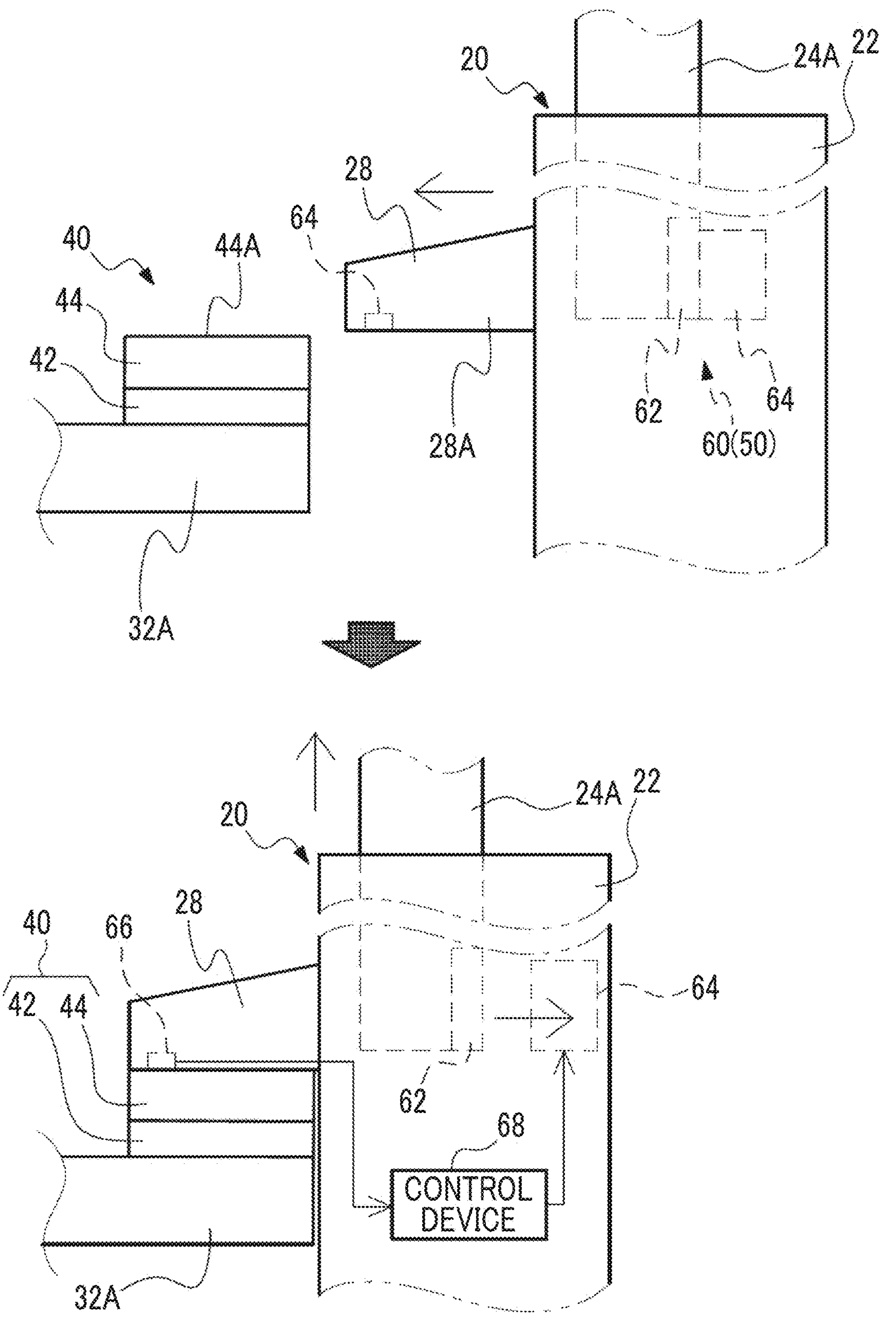
FIG. 5 is a partially enlarged view illustrating an example of the configuration of the radiography system according to the embodiment.

As shown in FIG. 5 as an example, the radiation source unit 20 according to the present embodiment comprises a restriction mechanism 50 that restricts the displacement of the arm 24. The restriction mechanism 50 includes an electromagnetic brake 60 as an example. The electromagnetic brake 60 includes a magnetization member 62 provided in the vertical portion 24A of the arm 24, and a magnet 64 that generates a magnetic force by energization. The magnetization member 62 and the magnet 64 are provided at opposite positions. In the electromagnetic brake 60, in a case where the magnetic force is generated in the magnet 64, the magnetic attraction is generated between the magnetization member 62 and the magnet 64. In addition, the magnet 64 is fixed to the main body portion 22. Therefore, the expansion and contraction of the arm 24 in the up-down direction with respect to the main body portion 22 is restricted. In such a manner, in a state in which the radiation source unit 20 is not attached to the decubitus table 30, the displacement of the arm 24 is restricted in the radiation source unit 20.

In addition, the radiation source unit 20 comprises a detection portion 66. The detection portion 66 is a sensor that can detect a state where the attachment portion 28 is attached to the decubitus table 30. In the example shown in FIG. 5, the detection portion 66 is provided in the attachment portion 28. Here, the attachment state with respect to the decubitus table 30 includes whether or not the attachment portion 28 is attached, a position where the attachment portion 28 is attached, and the like. The detection portion 66 is, for example, a mechanical switch in which a pressing portion protrudes from a lower surface 28A of the attachment portion 28. The detection portion 66 is an example of a "detection portion" according to the technique of the present disclosure.

Next, a description will be made of a state where the radiation source unit 20 is attached to the decubitus table 30 with reference to FIG. 5. In a case where the radiation source unit 20 is attached to the decubitus table 30, the radiation source unit 20 is moved toward the decubitus table 30. Then, as shown in the lower part of FIG. 5, the attachment portion 28 is placed on the stage member 44, whereby the radiation source unit 20 is attached to the decubitus table 30.

In a case where the radiation source unit 20 is attached to the decubitus table 30 through the attachment portion 28, the restriction on the displacement of the arm 24 is released. Specifically, in a case where the detection portion 66 detects that the attachment portion 28 is attached to the decubitus table 30, the restriction of the displacement of the arm 24 by the restriction mechanism 50 is released.

In the example shown in the lower part of FIG. 5, in a case where the attachment state is detected by the detection portion 66, a detection signal is output from the detection portion 66 to the control device 68. For example, in a case where the detection portion 66 is a mechanical switch, the mechanical switch is pressed in a case where the attachment portion 28 is placed on the stage member 44. Accordingly, a signal indicating that the attachment portion 28 is attached to the decubitus table 30 (that is, the attachment completion signal) is output from the mechanical switch to the control device 68. The attachment completion signal is, for example, a current value equal to or greater than a threshold value indicating an ON state.

The control device 68 is a device that controls the operation of the electromagnetic brake 60. The control device 68 is, for example, a computer including a processor, a storage, and a random access memory (RAM). In addition, as the control device 68, a device including an application specific integrated circuit (ASIC), a field-programmable gate array (FPGA), and/or a programmable logic device (PLD) may be applied instead of the computer. Further, a hardware configuration and a software configuration may be used in combination, instead of the computer. In addition, the control device 68 does not need to be a dedicated device that controls the electromagnetic brake 60, and a control device that controls the entire radiation source unit 20 may function as the control device 68.

The control device 68 acquires a signal indicating the attachment state of the attachment portion 28 from the detection portion 66. Moreover, the control device 68 outputs an operation signal to the electromagnetic brake 60 on the basis of the acquired signal. For example, in a case where the attachment completion signal is acquired from the detection portion 66, the control device 68 outputs a restriction release signal to the electromagnetic brake 60. The restriction release signal is a signal indicating an operation of releasing the magnetic attraction between the magnetization member 62 and the magnet 64.

In the electromagnetic brake 60, in a case where the restriction release signal is received, the magnetic attraction between the magnetization member 62 and the magnet 64 is eliminated. In addition, the magnet 64 is retracted to a position separated from the arm 24. Then, the arm 24 can be expanded and contracted in the up-down direction. In this way, in a case where the detection portion 66 detects that the attachment portion 28 is attached to the decubitus table 30, the restriction of the displacement of the arm 24 by the restriction mechanism 50 is released.

As described above, in the radiation source unit 20 according to the present second embodiment, the detection portion 66 is provided, and in the restriction mechanism 50, in a case where the detection portion 66 detects that the attachment portion 28 is attached to the decubitus table 30, the restriction on the displacement of the arm 24 can be released. Accordingly, the burden of the operation of the user is reduced as compared with a case where the attachment operation and the operation of releasing the restriction by the restriction mechanism 50 are separate from each other. That is, it is not necessary to confirm the release of the restriction of the arm 24 after the attachment operation. In addition, since the restriction on the displacement of the arm 24 can be controlled in accordance with the detection result of the detection portion 66, it is not necessary to incorporate a complicated mechanical mechanism in the radiation source unit 20, and the configuration of the radiation source unit 20 is simplified.

In the second embodiment, although a form example where the detection portion 66 is the mechanical switch is described, the technology of the present disclosure is not limited thereto. The detection portion 66 only needs to be capable of detecting the attachment state of the attachment portion 28 to the decubitus table 30. For example, the detection portion 66 may be a photoelectric sensor, a magnetic sensor, or a proximity sensor. These sensors are provided, for example, on a lower surface 28A of the attachment portion 28, and detect that the attachment portion 28 is placed on the stage member 44 to detect an attachment state of the attachment portion 28.

In addition, in the second embodiment, the form example has been described in which the detection portion 66 is provided in the attachment portion 28, but the technology of the present disclosure is not limited to this. For example, the detection portion 66 may be provided in addition to the attachment portion 28. For example, the detection portion 66 may be a distance measurement sensor provided on a surface of the main body portion 22 facing the decubitus table 30 (here, the left side surface). In this case, in a case where the distance between the decubitus table 30 and the main body portion 22 is equal to or smaller than a predetermined distance, the detection portion 66 may detect that the attachment portion 28 is attached to the decubitus table 30. However, since the detection portion 66 is provided in the attachment portion 28, it is easy to detect that the radiation source unit 20 is attached to the decubitus table 30. The reason for this is that the radiation source unit 20 is attached to the decubitus table 30 through the attachment portion 28, and thus the attachment state is easily detected as compared with other parts.

In addition, in the second embodiment, the form example has been described in which the restriction mechanism 50 is the electromagnetic brake 60, but the technology of the present disclosure is not limited to this. For example, the restriction mechanism 50 may be a brake mechanism other than the electromagnetic brake 60. In addition, the displacement of the arm 24 may be restricted by the engaging member 51 as described in the first embodiment. In this case, the restriction of the displacement of the arm 24 is released by driving the engaging member 51 in accordance with the detection result of the detection portion 66.

Modification Example

In the second embodiment, although a form example has been described in which the expanding and contracting of the arm 24 in the up-down direction is restricted, the technology of the present disclosure is not limited thereto. In the present modification example, the expansion and contraction of the arm 24 in the horizontal direction and/or the rotation of the arm 24 in the horizontal plane are restricted by the restriction mechanism 50.

Figure 6:
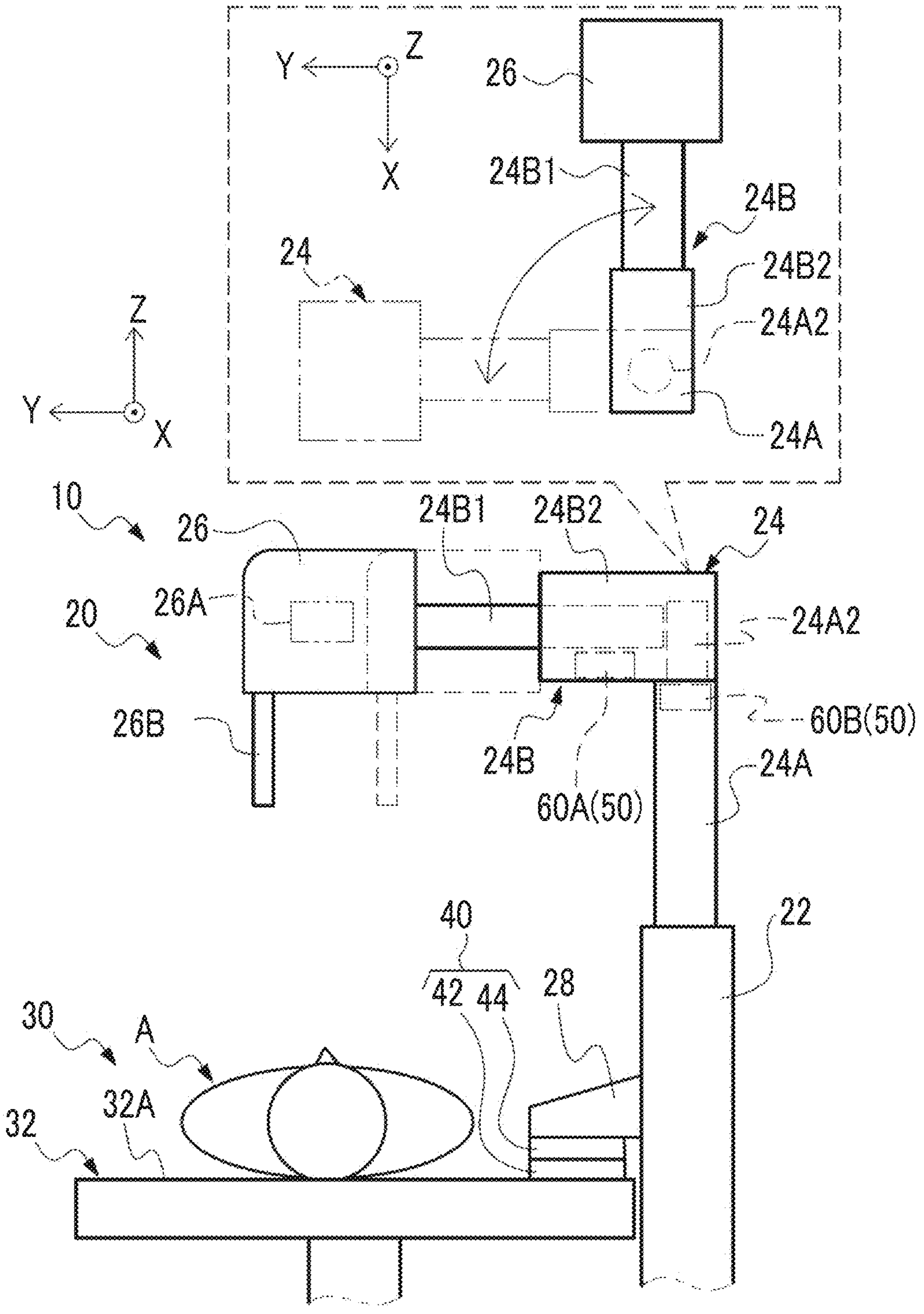
FIG. 6 is a schematic front view illustrating an example of the configuration of the radiography system according to the embodiment.

As shown in FIG. 6 as an example, the arm 24 can be expanded and contracted along a horizontal direction. Specifically, the horizontal portion 24B of the arm 24 is allowed to be expandable and contractible with respect to the vertical portion 24A. In the example shown in FIG. 6, the horizontal portion 24B includes a movable portion 24B1 and a fixing portion 24B2. The fixing portion 24B2 is a portion attached to the vertical portion 24A. The movable portion 24B1 is a portion that can be moved along the horizontal direction with respect to the fixing portion 24B2. The radiation irradiation portion 26 is provided in a distal end portion of the movable portion 24B1 (that is, an end portion on a side opposite to the fixing portion 24B2). The movable portion 24B1 is moved with respect to the fixing portion 24B2, so that the arm 24 can be expanded and contracted along the horizontal direction.

The electromagnetic brake 60A is provided in the horizontal portion 24B of the arm 24 as the restriction mechanism 50. In the example shown in FIG. 6, the electromagnetic brake 60A is provided inside the fixing portion 24B2.

Specifically, the electromagnetic brake 60A is provided inside the fixing portion 24B2 at a position facing the movable portion 24B1. Then, the electromagnetic brake 60A restricts the expansion and contraction of the arm 24 in the horizontal direction by magnetically attracting the base end portion (that is, the end portion on the side opposite to the distal end portion provided with the radiation irradiation portion 26) of the movable portion 24B1. In addition, since the configuration of the electromagnetic brake 60A is the same as the configuration of the electromagnetic brake 60 described above, the description thereof will not be repeated here.

In addition, the arm 24 is rotatable in a case where the radiation source unit 20 is viewed from above. Specifically, the horizontal portion 24B of the arm 24 is rotatable with respect to the vertical portion 24A in a horizontal plane. In the example shown in FIG. 6, the horizontal portion 24B is rotatable about the rotary shaft member 24A2 provided at the upper end of the vertical portion 24A. Here, the rotary shaft member 24A2 is a columnar member having a central axis along the up-down direction.

The electromagnetic brake 60B is provided in the vertical portion 24A of the arm 24 as the restriction mechanism 50. In the example shown in FIG. 6, the electromagnetic brake 60B is provided inside the vertical portion 24A. Specifically, the electromagnetic brake 60B is provided at a position facing the horizontal portion 24B in the vertical portion 24A. The electromagnetic brake 60B restricts the rotation of the arm 24 by magnetically attracting the lower surface of the horizontal portion 24B. In addition, since the configuration of the electromagnetic brake 60B is the same as the configuration of the electromagnetic brake 60 described above, the description thereof will not be repeated here.

Then, in a case where the radiation source unit 20 is attached to the decubitus table 30 through the attachment portion 28, the restriction on the displacement of the arm 24 is released. Specifically, in a case where the detection portion 66 detects that the attachment portion 28 is attached to the decubitus table 30, the restriction on the displacement of the arm 24 by the electromagnetic brakes 60A and 60B is released. Here, the expansion and contraction of the arm 24 in the horizontal direction is released, and the rotation of the arm 24 in a case where the radiation source unit 20 is viewed from above is released. The expansion and contraction of the arm 24 in the horizontal direction and the rotation of the arm 24 may be performed manually by the user or may be performed by a drive mechanism (not shown) provided in the arm 24.

As described above, in the radiation source unit 20 according to the present embodiment, the displacement of the arm 24 includes the expansion and contraction of the arm 24 including a component in the horizontal direction. In a case in which the arm 24 expands and contracts in the horizontal direction, the centroid of the radiation source unit 20 moves in the horizontal direction, and the posture of the radiation source unit 20 may be unstable. In the present configuration, the radiation source unit 20 is attached to the decubitus table 30 through the attachment portion 28, so that the restriction on the displacement of the arm 24 by the electromagnetic brake 60A is released. Therefore, it is realized that the arm 24 is expanded and contracted in a direction including a component in the horizontal direction in a state where the radiation source unit 20 is stable.

For example, in the decubitus imaging, imaging is performed in a state in which the radiation source 26A is positioned above the decubitus table 30 (that is, overhanging). In this case, the arm 24 is required to be expanded and contracted in the horizontal direction. In the present configuration, even in a case in which the displacement of the arm 24 includes the expansion and contraction including a component in the horizontal direction, the arm 24 can be displaced in a state in which the posture of the radiation source unit 20 is stable. In addition, it is easy to adjust the position of the radiation source 26A in the right-left direction.

In addition, in the radiation source unit 20 according to the present embodiment, the displacement of the arm 24 includes the rotation of the arm 24 in a case where the radiation source unit 20 is viewed from above. In a case in which the arm 24 is rotated, the centroid of the radiation source unit 20 is moved, and the posture of the radiation source unit 20 may be unstable. In the present configuration, the radiation source unit 20 is attached to the decubitus table 30 through the attachment portion 28, so that the restriction on the displacement of the arm 24 by the electromagnetic brake 60B is released. Therefore, it is realized to rotate the arm 24 in a stable state of the radiation source unit 20.

For example, in the decubitus imaging, the radiation source 26A may be temporarily retreated from above the decubitus table 30. In this case, it is required to rotate the arm 24 in a case where the radiation source unit 20 is viewed from above. In the present configuration, even in a case where the displacement of the arm 24 includes the rotation of the arm 24, the arm 24 can be displaced in a state in which the posture of the radiation source unit 20 is stable.

In the above-described modification example, although the form example has been described in which both the restriction of the expansion and contraction of the arm 24 in the horizontal direction and the restriction of the rotation of the arm 24 are released, the technology of the present disclosure is not limited to this. An aspect may be adopted in which any one of the restriction of the expansion and contraction of the arm 24 in the horizontal direction or the rotation of the arm 24 is released.

In addition, in the above-described modification example, the form example has been described in which the horizontal portion 24B of the arm 24 is rotated with respect to the vertical portion 24A, but the technology of the present disclosure is not limited to this. For example, the entire arm 24 may be rotated with respect to the main body portion 22.

In addition, in the second embodiment and the modification example, the displacement of the arm 24 restricted by the electromagnetic brakes 60, 60A, and 60B as the restriction mechanisms 50 may be any one of the expansion and contraction of the arm 24 in the up-down direction, the expansion and contraction of the arm 24 in the horizontal direction, and the rotation of the arm 24, or a combination of two or more of the expansion and contraction of the arm 24 in the up-down direction, the expansion and contraction of the arm 24 in the horizontal direction, and the rotation of the arm 24.

Third Embodiment

In the first embodiment, although a form example where the attachment portion 28 is placed on the stage member 44 of the guide mechanism 40 is described as an example of the form where the radiation source unit 20 is attached to the decubitus table 30, the technology of the present disclosure is not limited to this. In the present third embodiment, the radiation source unit 20 is attached to the decubitus table 30 through an attachment portion 70 including a plurality of contact portions 71.

Figure 7:
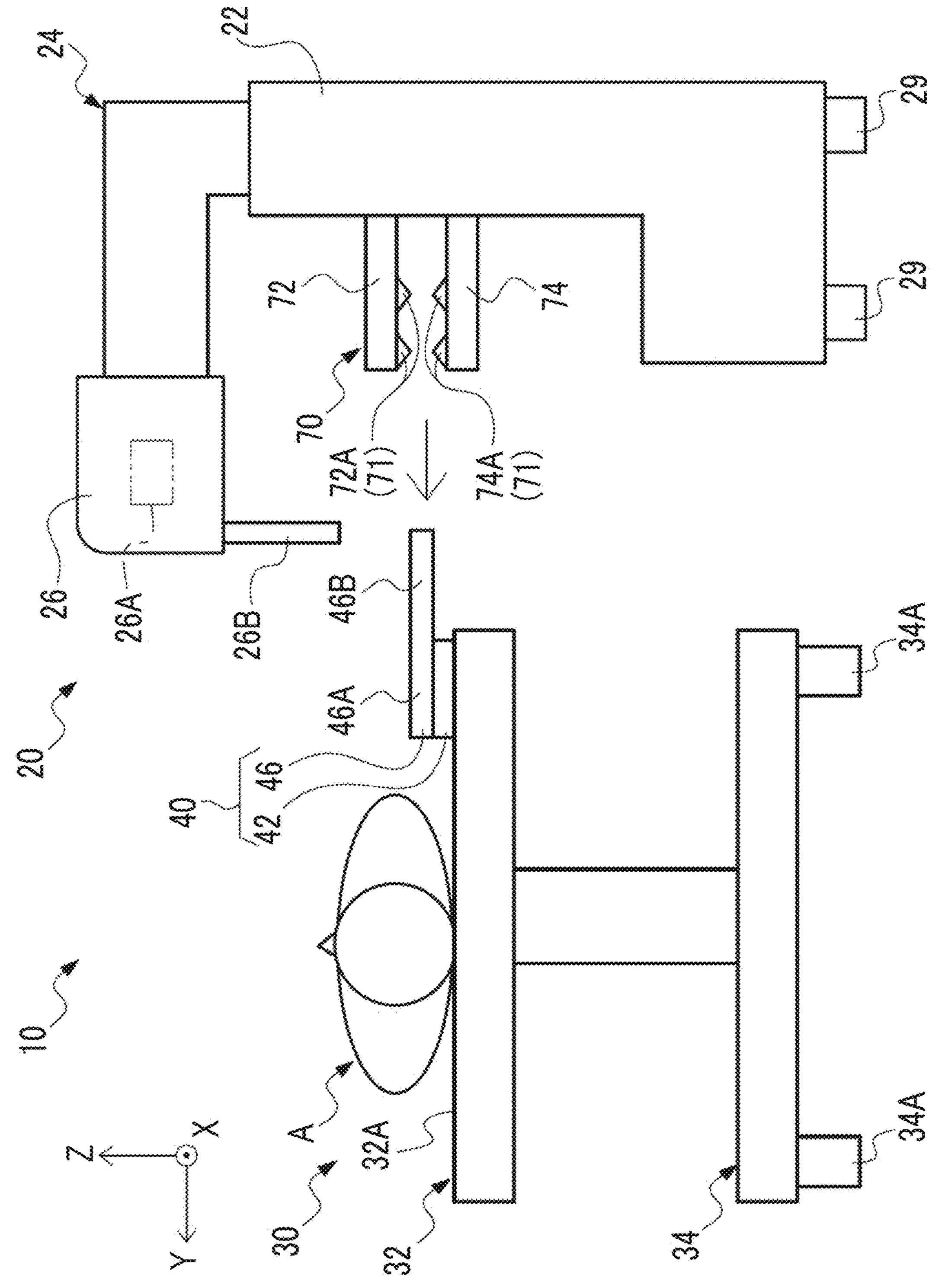
FIG. 7 is a schematic front view illustrating an example of the configuration of the radiography system according to the embodiment.
Figure 8:
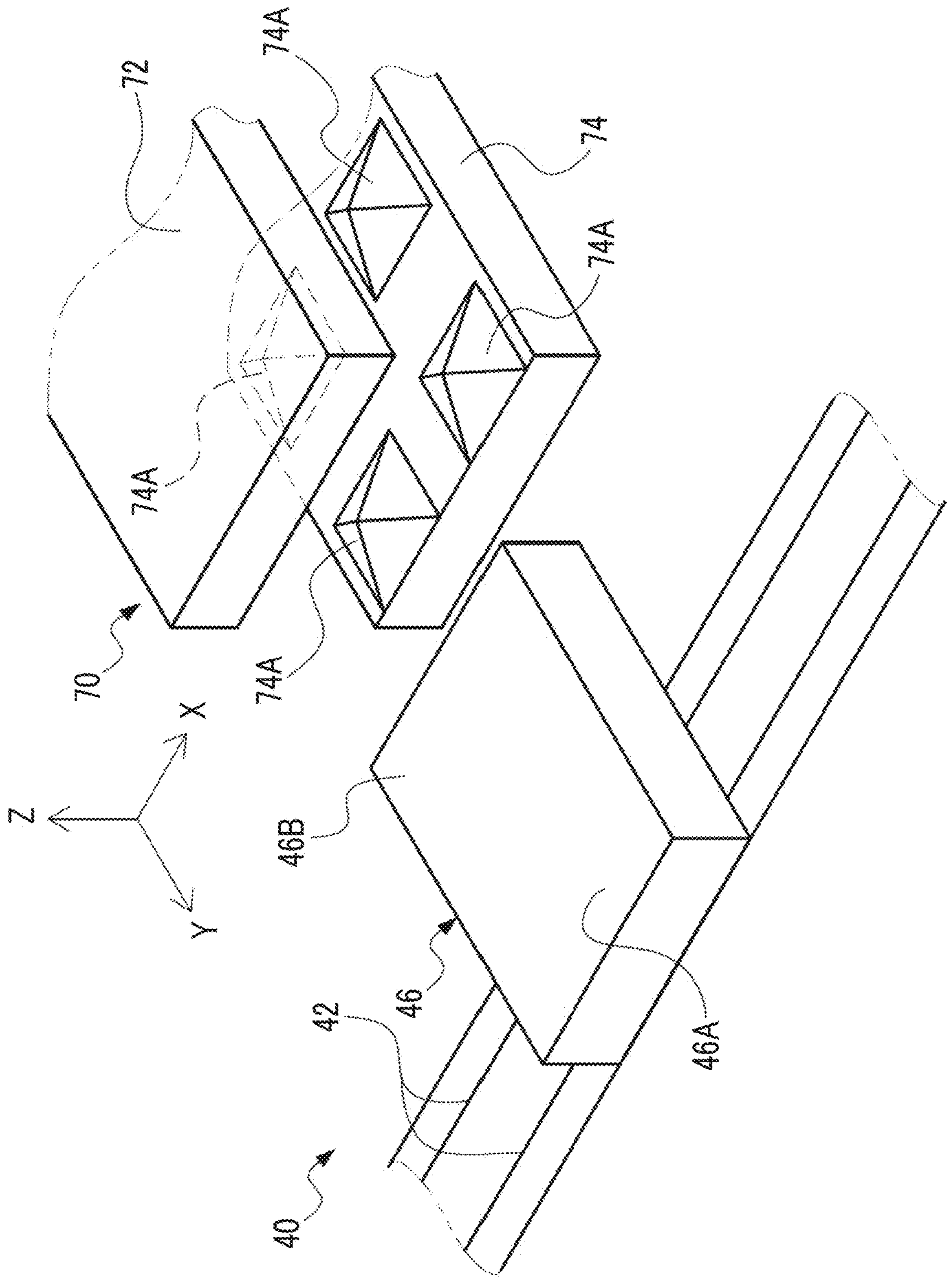
FIG. 8 is a partially perspective view illustrating an example of the configuration of the radiography system according to the embodiment.

As shown in FIGS. 7 and 8 as an example, the radiation source unit 20 comprises an attachment portion 70. The attachment portion 70 is provided on a surface of the main body portion 22 on the side of the decubitus table 30 (here, a left side surface). The attachment portion 70 includes a plurality of contact portions 71. The plurality of contact portions 71 support a rotational moment of the radiation source unit 20 in a direction in which the radiation source unit 20 falls in a state in which the radiation source unit 20 is attached to the decubitus table 30. The attachment portion 70 is an example of a "attachment portion" according to the technique of the present disclosure, and the plurality of contact portions 71 are an example of a "plurality of contact portions" according to the technique of the present disclosure.

The guide mechanism 40 is provided on the decubitus table 30. The guide mechanism 40 comprises a guide rail 42 and a support member 46 that is movable along the guide rail 42. The attachment portion 70 can be attached to the support member 46. The support member 46 is an example of a "support member" according to the technology of the present disclosure.

Specifically, the support member 46 includes a base portion 46A supported by the guide rail 42 and a protruding portion 46B protruding from the base portion 46A toward a side of the radiation source unit 20. In the example shown in FIG. 7, the support member 46 is a flat plate-shaped member. In addition, in the plate-shaped member, a portion supported from below by the guide rail 42 is the base portion 46A, and a portion protruding to the right side from the guide rail 42 is the protruding portion 46B.

In the example shown in FIG. 7, the attachment portion 70 has a pair of sandwiching portions 72 and 74. The pair of sandwiching portions 72 and 74 are plate-shaped portions that protrude from the radiation source unit 20. The pair of sandwiching portions 72 and 74 face each other in the up-down direction. A plurality of contact portions 71 are provided between the pair of sandwiching portions 72 and 74. The plurality of contact portions 71 provided between the pair of sandwiching portions 72 and 74 are brought into contact with the protruding portion 46B of the support member 46 in a state in which the radiation source unit 20 is attached to the decubitus table 30.

Specifically, a protrusion 72A is provided on the lower surface of the sandwiching portion 72. Further, a protrusion 74A is provided on an upper surface of the sandwiching portion 74. In the example shown in FIG. 8, four protrusions 74A are provided on the upper surface of the sandwiching portion 74. The four protrusions 74A are provided at positions corresponding to four corners of the sandwiching portion 74, respectively. The protrusion 74A has, for example, a quadrangular pyramid shape. In addition, although not shown, a protrusion 72A is also disposed on the lower surface of the sandwiching portion 72 in the same manner as the sandwiching portion 74. In this way, the attachment portion 70 is provided with a plurality of contact portions 71.

Figure 9:
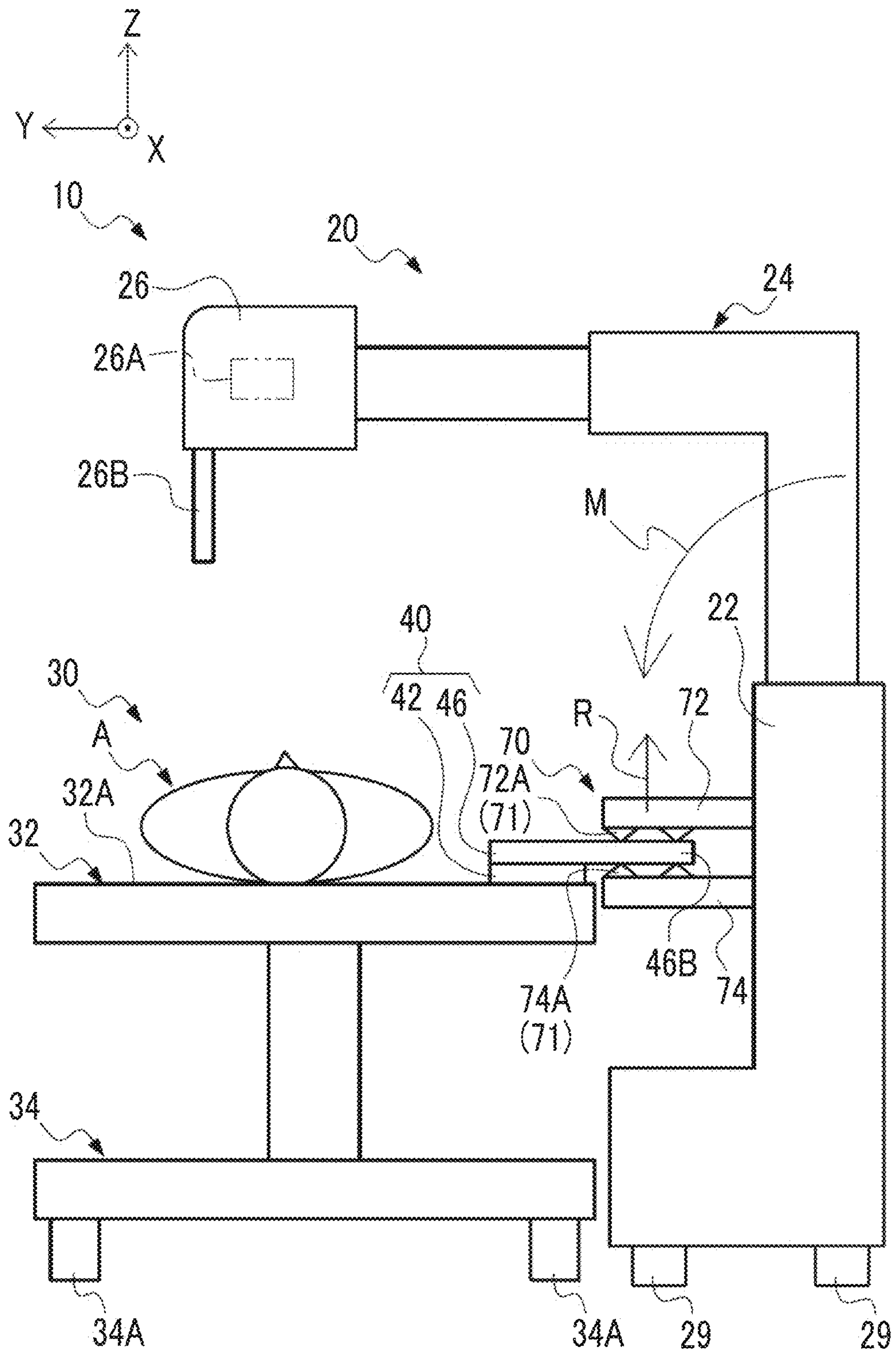
FIG. 9 is a schematic front view illustrating an example of a configuration of the radiography system according to the embodiment.

As shown in FIG. 9 as an example, the attachment portion 70 is attached to the support member 46. Specifically, the protruding portion 46B of the support member 46 is inserted between the pair of sandwiching portions 72 and 74. Then, the protrusion 72A of the sandwiching portion 72 comes into contact with the upper surface of the protruding portion 46B from above, and the protrusion 74A of the sandwiching portion 74 comes into contact with the lower surface of the protruding portion 46B from below. In this way, the attachment portion 70 is attached to the support member 46 by sandwiching the support member 46 in the up-down direction through the plurality of contact portions 71.

In a case where the attachment portion 70 is attached to the support member 46, as described above, the restriction on the displacement of the arm 24 is released. For example, in a case where the detection portion 66 (see FIG. 5 and the like) detects that the plurality of contact portions 71 are in contact with the support member 46, the restriction of the displacement of the arm 24 by the restriction mechanism 50 (see FIG. 5 and the like) is released. Here, in the example shown in FIG. 9, the arm 24 is extended in the up-down direction and is further extended in the horizontal direction (here, the left direction). Accordingly, since the centroid of the radiation source unit 20 moves to the upper left, the posture of the radiation source unit 20 is destabilized. Specifically, a rotational moment around the centroid of the radiation source unit 20 is generated by the load of the radiation irradiation portion 26. This rotational moment is a rotational moment in a direction in which the radiation source unit 20 falls. In the example shown in FIG. 9, a rotational moment M in a direction in which the radiation source unit 20 falls toward the decubitus table 30 (here, counterclockwise as viewed from the paper surface side of FIG. 9) is generated.

In a case where the rotational moment M acts on the radiation source unit 20, the plurality of contact portions 71 support the rotational moment M in the attachment portion 70. Specifically, a reaction force R is generated with respect to the attachment portion 70 by the contact between the plurality of contact portions 71 and the support member 46. In the example shown in FIG. 9, a reaction force R is generated with respect to the attachment portion 70 by the contact between the protrusion 72A and the protruding portion 46B. The reaction force R acts in a direction in which the rotational moment M in the direction in which the above-described radiation source unit 20 falls is canceled. In addition, since a plurality of protrusions 72A are provided, a reaction force R is generated in contact with a plurality of positions. In this way, in the attachment portion 70, the plurality of contact portions 71 support the rotational moment M in the direction in which the radiation source unit 20 falls.

As described above, in the radiation source unit 20 according to the present embodiment, the plurality of contact portions 71 are provided in the attachment portion 70, and in a state in which the radiation source unit 20 is attached to the decubitus table 30, the plurality of contact portions 71 support the rotational moment M of the radiation source unit 20 in the falling direction. Accordingly, the radiation source unit 20 is stable even in a state where the arm 24 is displaced in various ways as compared with a case where the radiation source unit 20 is supported at one point. For example, in a case in which the position of the radiation irradiation portion 26 is changed by displacing the arm 24, the position of the centroid of the radiation source unit 20 is changed, and the magnitude of the rotational moment M is also changed. In the present configuration, since the plurality of contact portions 71 support the rotational moment M, it is possible to cope with the displacement of the various arms 24 and contribute to the stabilization of the posture of the radiation source unit 20.

In addition, in the radiation source unit 20 according to the present embodiment, the support member 46 to which the attachment portion 70 can be attached is provided on the decubitus table 30, and the attachment portion 70 is attached to the support member 46 by sandwiching the support member 46 from the up-down direction through the plurality of contact portions 71. Accordingly, the radiation source unit 20 is more stable in a state where the arm 24 is displaced in various ways as compared with a case where the radiation source unit 20 is supported by the attachment portion 70 only from one of the up-down directions. For example, in a case where the position of the radiation irradiation portion 26 is changed by displacing the arm 24, the direction of the rotational moment M may be reversed. In the present configuration, since the support member 46 is sandwiched in the up-down direction, it is possible to cope with the displacement of the various arms 24 and contribute to stabilization of the posture of the radiation source unit 20.

In the present third embodiment, although an example in which the plurality of contact portions 71 have the quadrangular pyramid-shaped protrusions has been described, the technology of the present disclosure is not limited thereto. For example, the plurality of contact portions 71 may be conical or hemispherical protrusions. In addition, the number and arrangement of the plurality of contact portions 71 are not particularly limited as long as the plurality of contact portions 71 can support the rotational moment M.

In addition, in the present third embodiment, although a form example where the support member 46 is a plate-shaped member and is sandwiched by the attachment portion 70 has been described, the technology of the present disclosure is not limited to this. For example, the support member 46 may be a columnar member, and the attachment portion 70 may be a cylindrical member. In this case, the support member 46 having a columnar shape is inserted into the cylindrical attachment portion 70, whereby the attachment portion 70 is attached to the support member 46.

In each of the above embodiments, although a form example where the arm 24 expands and contracts independently in the up-down direction and the horizontal direction is described, the technology of the present disclosure is not limited to this. For example, the arm 24 may have an aspect in which the arm 24 is expanded and contracted in the up-down direction and the horizontal direction at the same time. That is, the arm 24 may be configured to expand and contract along an oblique direction in which the arm 24 is inclined toward the decubitus table 30 from the up-down direction.

Figure 10:
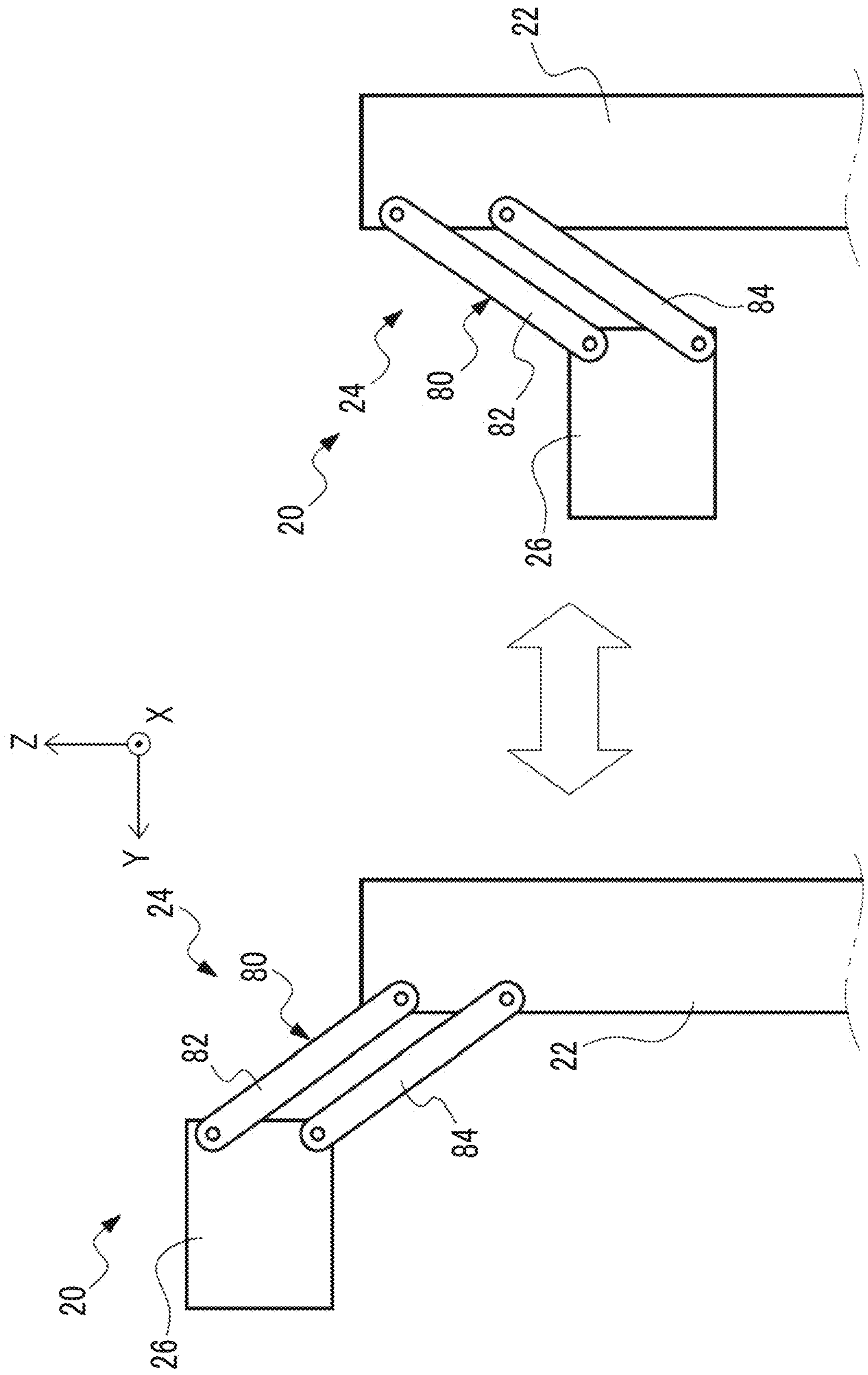
FIG. 10 is a schematic front view illustrating an example of a configuration of a radiation source unit according to the embodiment.

In addition, the displacement of the arm 24 may include inclination of the arm 24 in addition to the expansion and contraction of the arm 24. As shown in FIG. 10 as an example, the arm 24 may include a link mechanism 80. The link mechanism 80 includes a pair of link arms 82 and 84. One end of each of the pair of link arms 82 and 84 is rotationally movably attached to the main body portion 22, and the other end thereof is rotationally movably attached to the radiation irradiation portion 26. The arm 24 can also be displaced by the displacement of the link mechanism 80. In the example shown in FIG. 10, an example in which the link mechanism 80 is rotationally moved counterclockwise is shown. In this case, the restriction mechanism 50 restricts the rotational movement of the link arms 82 and 84 in the link mechanism 80 to restrict the displacement of the arm 24.

Figure 11:
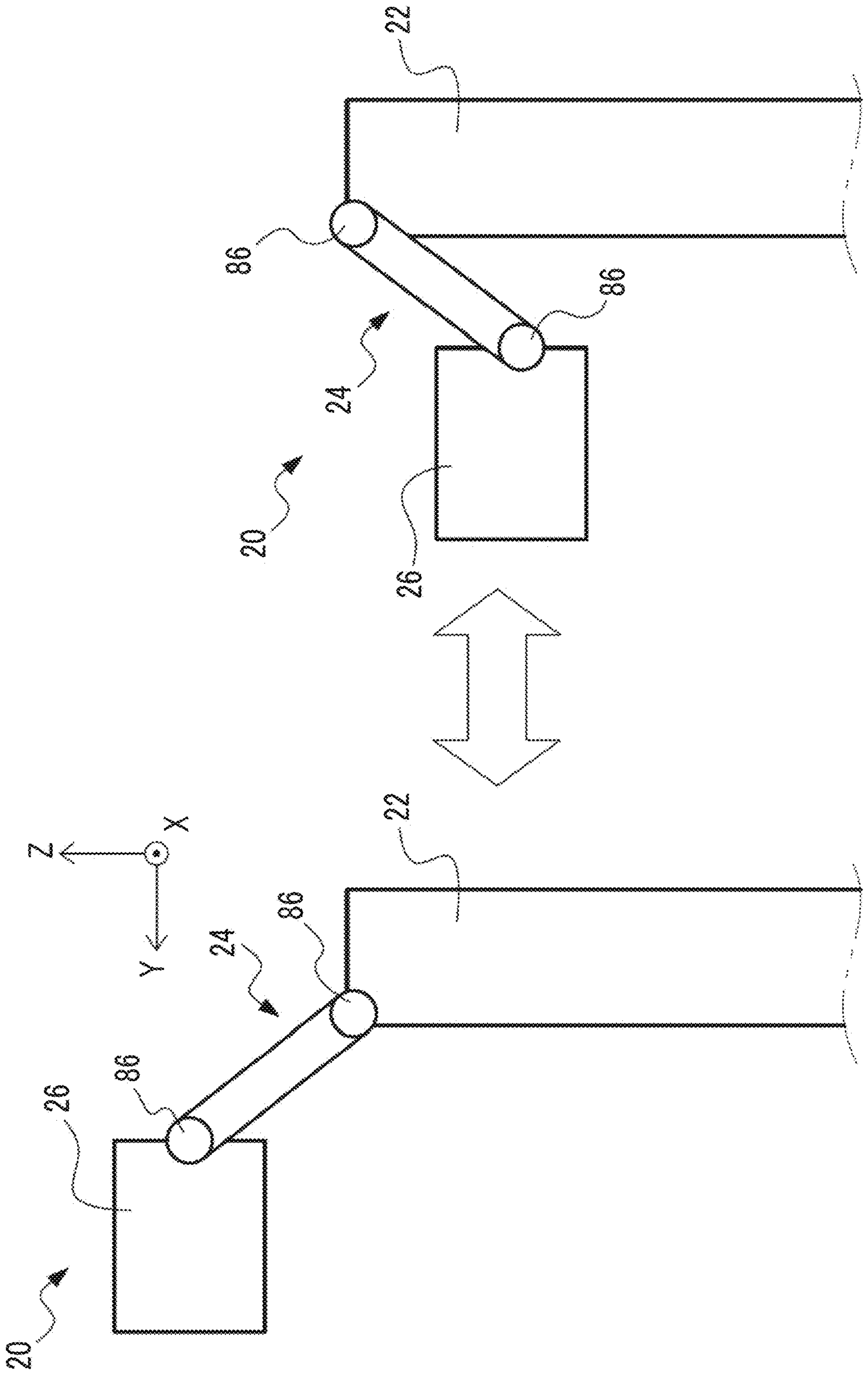
FIG. 11 is a schematic front view illustrating an example of the configuration of the radiation source unit according to the embodiment.

In addition, as shown in FIG. 11 as an example, the arm 24 may include a joint mechanism 86. The joint mechanism 86 is a mechanism capable of rotationally moving the arm 24, and is, for example, a universal joint. The arm 24 is attached to each of the main body portion 22 and the radiation irradiation portion 26 through a joint mechanism 86. The arm 24 can be rotationally moved with respect to the main body portion 22 and the radiation irradiation portion 26. In the example shown in FIG. 11, an example in which the arm 24 is rotationally moved counterclockwise about the joint mechanism 86 attached to the main body portion 22 as a starting point is shown. In this case, the displacement of the arm 24 is restricted by restricting the rotational movement of the joint mechanism 86 by the restriction mechanism 50.

Figure 12:
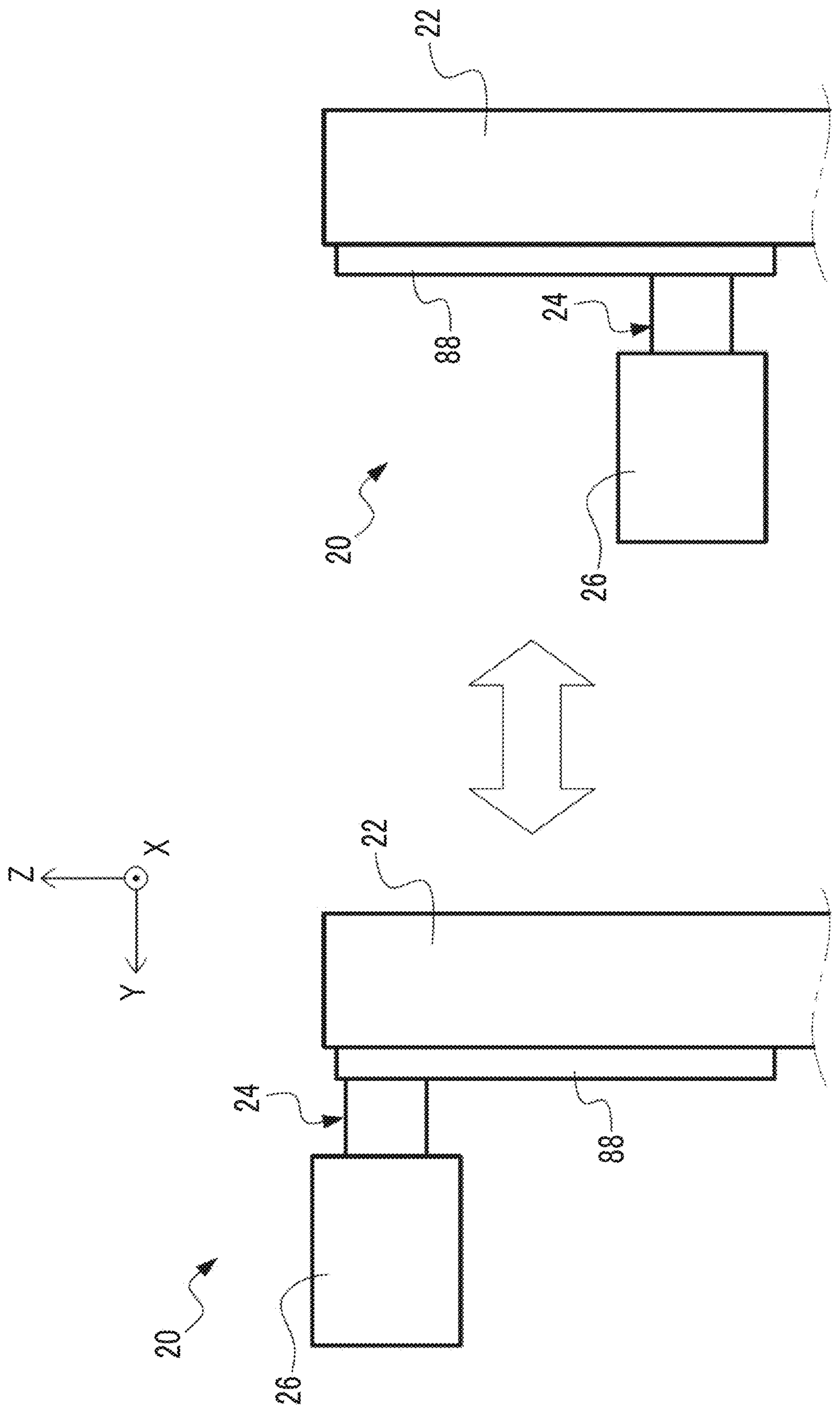
FIG. 12 is a schematic front view illustrating an example of the configuration of a radiation source unit according to the embodiment.

In addition, as shown in FIG. 12 as an example, the arm 24 may be attached to the main body portion 22 through a slide mechanism 88. The slide mechanism 88 is a guide mechanism for linearly moving the arm 24. The proximal end side of the arm 24 is slidably attached to the slide mechanism 88. The arm 24 can be linearly moved with respect to the main body portion 22 along the sliding mechanism 88. In the example shown in FIG. 12, the slide mechanism 88 is provided on a surface of the main body portion 22 on the side of the decubitus table 30 (here, a left surface), and the arm 24 is displaceable in the up-down direction along the slide mechanism 88. In this case, the restriction mechanism 50 restricts the displacement of the arm 24 by locking the arm 24 in the slide mechanism 88.

In addition, in each of the above embodiments, the form example has been described in which the guide rail 42 of the guide mechanism 40 is provided along the longitudinal direction of the decubitus table 30, but the technology of the present disclosure is not limited to this. For example, the guide rail 42 may be in an aspect of extending along the lateral direction of the decubitus table 30. In addition, the guide mechanism 40 may not be provided on the placement surface 32A of the decubitus table 30, or may be attached below the placement portion 32 through a dedicated member.

In addition, in each of the embodiments described above, the form example has been described in which the decubitus table 30 is the dedicated bed for radiography, but the technology of the present disclosure is not limited to this. The decubitus table 30 may be a bed provided in a general ward or a general examination table. In this case, the guide mechanism 40 is separately attached to the decubitus table 30.

The described contents and the illustrated contents are detailed explanations of a part according to the technique of the present disclosure, and are merely examples of the technique of the present disclosure. For example, the descriptions regarding the configurations, the functions, the actions, and the effects are descriptions regarding an example of the configurations, the functions, the actions, and the effects of the part according to the present disclosed technology. Accordingly, in the contents described and the contents shown hereinabove, it is needless to say that removal of an unnecessary part, or addition or replacement of a new element may be employed within a range not departing from the gist of the present disclosed technology. In addition, in order to avoid complication and facilitate the understanding of a portion according to the present disclosed technology, regarding the contents described and illustrated above, description related to common technical knowledge or the like which does not need to be described to enable implementation of the present disclosed technology has been omitted.

In the present specification, "A and/or B" is synonymous with "at least one of A or B". That is, "A and/or B" means that only A may be used, only B may be used, or a combination of A and B may be used. In the present specification, the same approach as "A and/or B" also applies to an expression of three or more matters connected with "and/or".

All documents, patent applications, and technical standards disclosed in the present specification are incorporated in the present specification by reference to the same extent as those in a case where each of the documents, patent applications, and technical standards are specifically and individually indicated to be incorporated by reference.

Regarding the above-described embodiment, the following supplementary notes will be further disclosed.

Supplementary Note 1

A radiation irradiation apparatus that is configured to independently travel from a decubitus table on which a subject is capable being placed, including:

an attachment portion that allows the radiation irradiation apparatus to be attached to and detached from the decubitus table;

a radiation irradiation portion capable of emitting radiation to the subject;

a holding portion that is provided at a distal end portion thereof with the radiation irradiation portion and that holds the radiation irradiation portion to be displaceable; and a restriction mechanism that restricts displacement of the holding portion, in which the radiation irradiation apparatus is attached to the decubitus table through the attachment portion to release restriction of the displacement in the restriction mechanism.

Supplementary Note 2

The radiation irradiation apparatus according to Supplementary Note 1, in which the displacement includes movement of the holding portion including a component in an up-down direction.

Supplementary Note 3

The radiation irradiation apparatus according to Supplementary Note 1 or 2, in which the displacement includes movement of the holding portion including a component in a horizontal direction.

Supplementary Note 4

The radiation irradiation apparatus according to any one of Supplementary Notes 1 to 3, in which the displacement includes rotation of the holding portion in a case in which the radiation irradiation apparatus is viewed from above.

Supplementary Note 5

The radiation irradiation apparatus according to any one of Supplementary Notes 1 to 4, in which the restriction mechanism includes an engaging member that is engageable with the holding portion, and the restriction of the displacement is released by engagement of the engaging member with the holding portion in conjunction with an attachment operation through the attachment portion.

Supplementary Note 6

The radiation irradiation apparatus according to Supplementary Note 5, in which the decubitus table includes a guide mechanism that allows the radiation irradiation apparatus attached to the attachment portion to be movable with respect to the decubitus table, the guide mechanism includes a guide rail extending along a movement direction of the radiation irradiation apparatus, and a moving member that is movable along the guide rail, the attachment portion is attached to the moving member, and a release member provided in the moving member directly or indirectly displaces the engaging member to release the engagement of the engaging member with the holding portion.

Supplementary Note 7

The radiation irradiation apparatus according to any one of Supplementary Notes 1 to 3, further including:

a detection portion capable of detecting a state in which the attachment portion is attached to the decubitus table, in which the restriction mechanism is capable of releasing restriction of the displacement in a case in which the detection portion detects that the attachment portion is attached to the decubitus table.

Supplementary Note 8

The radiation irradiation apparatus according to any one of Supplementary Notes 1 to 7, in which the attachment portion has a plurality of contact portions, and the plurality of contact portions support a rotational moment of the radiation irradiation apparatus in a falling direction in a state in which the radiation irradiation apparatus is attached to the decubitus table through the attachment portion.

Supplementary Note 9

The radiation irradiation apparatus according to Supplementary Note 8, in which the decubitus table is provided with a support member to which the attachment portion is attachable, and the attachment portion is attached to the support member by sandwiching the support member from an up-down direction through the plurality of contact portions.

Supplementary Note 10

A radiography system including:

the radiation irradiation apparatus any one of Supplementary Notes 1 to 9; and a decubitus table to which the radiation irradiation apparatus is attachable.

What is claimed is:

1. A radiation irradiation apparatus that is configured to independently travel from a decubitus table on which a subject is capable being placed, comprising:

an attachment portion that allows the radiation irradiation apparatus to be attached to and detached from the decubitus table;

a radiation irradiation portion capable of emitting radiation to the subject;

a holding portion that is provided at a distal end portion thereof with the radiation irradiation portion and that holds the radiation irradiation portion to be displaceable; and a restriction mechanism that restricts displacement of the holding portion, wherein the restriction mechanism includes an engaging member engageable with the holding portion to restrict the displacement of the holding portion, and wherein, in conjunction with an attachment operation in which the radiation irradiation apparatus is attached to the decubitus table through the attachment portion, engagement between the engaging member and the holding portion is released to release the restriction of the displacement of the holding portion.

2. The radiation irradiation apparatus according to claim 1, wherein the displacement includes movement of the holding portion including a component in an up-down direction.

3. The radiation irradiation apparatus according to claim 1, wherein the displacement includes movement of the holding portion including a component in a horizontal direction.

4. The radiation irradiation apparatus according to claim 1, wherein the displacement includes rotation of the holding portion about a vertical axis.

5. The radiation irradiation apparatus according to claim 1, wherein the decubitus table includes a guide mechanism that allows the radiation irradiation apparatus attached to the attachment portion to be movable with respect to the decubitus table, the guide mechanism includes a guide rail extending along a movement direction of the radiation irradiation apparatus, and a moving member that is movable along the guide rail, the attachment portion is attached to the moving member, and a release member provided in the moving member directly or indirectly displaces the engaging member to release the engagement between the engaging member and the holding portion.

6. The radiation irradiation apparatus according to claim 1, wherein the attachment portion has a plurality of contact portions, and the plurality of contact portions support a rotational moment of the radiation irradiation apparatus in a falling direction in a state in which the radiation irradiation apparatus is attached to the decubitus table through the attachment portion.

7. A radiography system comprising:

the radiation irradiation apparatus according to claim 1; and a decubitus table to which the radiation irradiation apparatus is attachable.

8. The radiation irradiation apparatus according to claim 6, wherein the decubitus table is provided with a support member to which the attachment portion is attachable, and the attachment portion is attached to the support member by sandwiching the support member from an up-down direction through the plurality of contact portions.

* * * * *